US012630828B2

(12) United States Patent
Mueller

(10) Patent No.: US 12,630,828 B2
(45) Date of Patent: May 19, 2026

(54) APTAMERS FOR USE AGAINST AUTOANTIBODY-ASSOCIATED DISEASES

(71) Applicant: Berlin Cures Holding AG, Zurich (CH)

(72) Inventor: Johannes Mueller, Berlin (DE)

(73) Assignee: APTA Therapeutics GmbH, Berlin (DE)

( * ) Notice: Subject to any disclaimer, the term of this patent is extended or adjusted under 35 U.S.C. 154(b) by 0 days.

(21) Appl. No.: 15/501,238

(22) PCT Filed: Aug. 4, 2015

(86) PCT No.: PCT/EP2015/067951
§ 371 (c)(1),
(2) Date: Feb. 2, 2017

(87) PCT Pub. No.: WO2016/020377
PCT Pub. Date: Feb. 11, 2016

(65) Prior Publication Data
US 2017/0226513 A1 Aug. 10, 2017

(30) Foreign Application Priority Data

Aug. 4, 2014 (EP) ..................................... 14179715

(51) Int. Cl.
*C12N 15/115* (2010.01)
*G01N 33/68* (2006.01)
*G16B 99/00* (2019.01)

(52) U.S. Cl.
CPC ....... *C12N 15/115* (2013.01); *G01N 33/6854* (2013.01); *G16B 99/00* (2019.02); *C12N 2310/16* (2013.01); *C12N 2330/00* (2013.01)

(58) Field of Classification Search
CPC .............. C12N 15/115; C12N 2310/16; C12N 2330/00; G01N 33/6854; G16B 99/00; Y02A 90/10; A61P 1/00; A61P 1/02; A61P 3/00; A61P 9/00; A61P 9/10; A61P 9/12; A61P 11/00; A61P 13/08; A61P 13/12; A61P 17/00; A61P 17/14; A61P 25/04; A61P 25/06; A61P 25/08; A61P 25/16; A61P 25/24; A61P 25/28; A61P 27/06; A61P 37/02; A61P 37/06; A61P 43/00
See application file for complete search history.

(56) References Cited

U.S. PATENT DOCUMENTS

| | | | | |
|---|---|---|---|---|
| 7,314,926 B1 * | 1/2008 | Miller | ................ | A61K 31/7088 |
| | | | | 536/23.1 |
| 8,144,850 B2 | 3/2012 | Brown et al. | | |
| 9,234,201 B2 | 1/2016 | Schimke et al. | | |
| 10,266,830 B2 | 4/2019 | Schimke et al. | | |
| 2005/0187176 A1 * | 8/2005 | Bates | ................... | C12N 15/115 |
| | | | | 514/44 R |
| 2009/0131351 A1 | 5/2009 | Green et al. | | |
| 2014/0155466 A1 * | 6/2014 | Schimke | ................. | A61P 25/00 |
| | | | | 422/69 |

FOREIGN PATENT DOCUMENTS

| | | | |
|---|---|---|---|
| CN | 103608456 A | 2/2014 |
| EP | 3177723 B1 | 12/2017 |
| JP | 2002-504490 A | 2/2002 |
| JP | 2005-500253 A | 1/2005 |
| JP | 2009-508473 A | 3/2009 |
| JP | 2014-509849 A | 4/2014 |
| JP | 2017-526761 A | 9/2017 |
| WO | 199965928 A2 | 12/1999 |
| WO | 2000061597 A1 | 10/2000 |
| WO | 2011133142 A1 | 10/2011 |
| WO | 2012000889 A1 | 1/2012 |
| WO | 2012119938 A2 | 9/2012 |

OTHER PUBLICATIONS

Haberland, A., Wallukat, G., Dahmen, C., Kage, A. & Schimke, I. Aptamer neutralization of beta 1-adrenoceptor autoantibodies isolated from patients with cardiomyopathies. Circulation Research 109, 986-992 (2011).*
Haberland, A. et al. Neutralization of pathogenic beta1-receptor autoantibodies by aptamers in vivo: The first successful proof of principle in spontaneously hypertensive rats. Molecular and Cellular Biochemistry 393, 177-180 (2014).*
Haberland, A. et al. Aptamer BC 007—A broad spectrum neutralizer of pathogenic autoantibodies against G-protein-coupled receptors. European Journal of Pharmacology 789, 37-45 (2016).*
Hernandez, L., Machado, I., Schafer, T. & Hernandez, F. Aptamers Overview: Selection, Features and Applications. Current Topics in Medicinal Chemistry 15, 1066-1081 (2015).*

(Continued)

*Primary Examiner* — Nancy J Leith
*Assistant Examiner* — Ruth Sophia Arieti
(74) *Attorney, Agent, or Firm* — Eversheds-Sutherland (US) LLP

(57) ABSTRACT

The present invention relates to new aptamer molecules for use in the treatment and/or diagnosis of autoimmune diseases associated with autoantibodies against G-protein coupled receptors, a pharmaceutical composition comprising such aptamer molecules, an apheresis column comprising such aptamer molecules and a method for the determination of nucleotide sequences for use as sequences of aptamer molecules.

5 Claims, 21 Drawing Sheets

Specification includes a Sequence Listing.

(56)　　　　　References Cited

OTHER PUBLICATIONS

Ismail, S. I. & Alshaer, W. Therapeutic aptamers in discovery, preclinical and clinical stages. Advanced Drug Delivery Reviews 134, 51-64 (2018).*

Katilius, E., Flores, C. & Woodbury, N. W. Exploring the sequence space of a DNA aptamer using microarrays. Nucleic Acids Research 35, 7626-7635 (2007).*

Li, B. Q. et al. Prediction of aptamer-target interacting pairs with pseudo-amino acid composition. PloS ONE 9, 1-7 (2014).*

Müller, J. et al. The DNA-Based Drug BC 007 neutralizes agonistically acting autoantibodies directed against G protein-coupled receptors Successful mode of action demonstrated in clinical phase 1 trial. Chemistry Today—Oligonucleotides & Peptides 37, 65-67 (2019).*

Nimjee, S. M., White, R. R., Becker, R. C. & Sullenger, B. A. Aptamers as Therapeutics. Annual Review of Pharmacology and Toxicology 57, 61-79 (2017).*

Sundaram, P., Kurniawan, H., Byrne, M. E. & Wower, J. Therapeutic RNA aptamers in clinical trials. European Journal of Pharmaceutical Sciences 48, 259-271 (2013).*

Yang, X., Li, N. & Gorenstein, D. G. Strategies for the discovery of therapeutic aptamers. Expert Opinion on Drug Discovery 6, 75-87 (2011).*

Zhou, J. & Rossi, J. Aptamers as targeted therapeutics: Current potential and challenges. Nature Reviews Drug Discovery 16, 181-202 (2017).*

Hakak, Y.; Shrestha, D.; Goegel, M. C.; Behan, D. P.; Chalmers, D. T. Global Analysis of G-Protein-Coupled Receptor Signaling in Human Tissues. FEBS Letters 2003, 550 (1-3), 11-17.*

Maier, H. J.; Schips, T. G.; Wietelmann, A.; Kruger, M.; Brunner, C.; Sauter, M.; Klingel, K.; Böttger, T.; Braun, T.; Wirth, T. Cardiomyocyte-Specific IκB Kinase (IKK)/NF-KB Activation Induces Reversible Inflammatory Cardiomyopathy and Heart Failure. Proceedings of the National Academy of Sciences USA 2012, 109 (29), 11794-11799.*

Bacher, S.; Schmitz, M. The NF-KB Pathway as a Potential Target for Autoimmune Disease Therapy. CPD 2004, 10 (23), 2827-2837.*

Unal, H.; Jagannathan, R.; Karnik, S. S. Mechanism of GPCR-Directed Autoantibodies in Diseases. In Biochemical Roles of Eukaryotic Cell Surface Macromolecules; Sudhakaran, P. R., Surolia, A., Eds.; Advances in Experimental Medicine and Biology; Springer New York: New York, NY, 2012; vol. 749, pp. 187-199.*

Xia, Y.; Kellems, R. E. Receptor-Activating Autoantibodies and Disease: Preeclampsia and Beyond. Expert Review of Clinical Immunology 2011, 7 (5), 659-674.*

Düngen, H.-D.; Dordevic, A.; Felix, S. B.; Pieske, B.; Voors, A. A.; McMurray, J. J. V.; Butler, J. B1-Adrenoreceptor Autoantibodies in Heart Failure: Physiology and Therapeutic Implications. Circulation: Heart Failure 2020, 13, e006155:1-9.*

Müller, J.; Wallukat, G.; Schimke, I. Autoantibody-Directed Therapy in Cardiovascular Diseases. Chapter 27 of The Heart in Rheumatic, Autoimmune and Inflammatory Diseases; Elsevier, 2017; pp. 659-679.*

Santosh, B.; Yadava, P. K. Nucleic Acid Aptamers: Research Tools in Disease Diagnostics and Therapeutics. BioMed Research International 2014, 540451:1-13.*

Ni, S.; Zhuo, Z.; Pan, Y.; Yu, Y.; Li, F.; Liu, J.; Wang, L.; Wu, X.; Li, D.; Wan, Y.; Zhang, L.; Yang, Z.; Zhang, B.-T.; Lu, A.; Zhang, G. Recent Progress in Aptamer Discoveries and Modifications for Therapeutic Applications. ACS Applied Materials & Interfaces 2021, 13 (8), 9500-9519.*

Tang and Insel. 2005. Genetic variation in G-protein-coupled receptors-consequences for G-protein-coupled receptors as drug targets. Exp. Opin. Therapeut. Targ. 9[6]:1247-1265 (Year: 2005).*

Rosenbaum et al. 2009. The structure and function of G-protein-coupled receptors. Nature 459[21]:356-363 (Year: 2009).*

Keefe et al. 2010. Aptamers as therapeutics. Nat. Rev. Drug Discov. 9:537-550 (Year: 2010).*

Lakhin et al. 2013. Aptamers: Problems, Solutions and Prospects. Acta naturae 5[4{19}]: 34-43 (Year: 2013).*

Santosh B. et al. 2014. Nucleic acid aptamers: research tools in disease diagnostics and therapeutics. Biomed Res Int 2014:540451 of Record (Year: 2014).*

Zhou and Rossi. 2016. Aptamers as targeted therapeutics: current potential and challenges. Drug Discov. 16:181-202 (Year: 2016).*

Watson et al. 2017. The Individual and Population Genetics of Antibody Immunity. Trends Immunol. 38[7]:459-470 (Year: 2017).*

Euesden et al. 2017. A bidirectional relationship between depression and the autoimmune disorders—New perspectives from the National Child Development Study. PLoS One 12[3]:e0173015 (Year: 2017).*

Latorraca et al. 2017. GPCR Dynamics: Structures in Motion. Chem. Rev. 117:139-155 (Year: 2017).*

Morita et al. 2018. Aptamer Therapeutics in Cancer: Current and Future. Cancers 10:80 (Year: 2018).*

Jiang et al. 2018. The Challenge of the Pathogenesis of Parkinson's Disease: Is Autoimmunity the Culprit? Frontiers Immunol. 9: 2047 (Year: 2018).*

Marks and Deane. 2020. How repertoire data are changing antibody science. J. Biol. Chem. 295[29]:9823-9837 (Year: 2020).*

Bognar and Gyurcsanyi. 2020. Aptamers against Immunoglobulins: Design, Selection and Bioanalytical Applications. Int. J. Mol. Sci. 21[16]:5748 (Year: 2020).*

Nussinovitch (and Shoenfeld. 2010. The Clinical Significance of Anti-Beta-1 Adrenergic Receptor Autoantibodies in Cardiac Disease. Clin. Rev. Allerg. Immunol. 44:75-83) (Year: 2010).*

Caja (et al. 2011. Antibodies in celiac disease: implications beyond diagnostics. Cellular Molec. Immunol. 8:103-109) (Year: 2011).*

Hoftberger (et al. 2022. Pathogenic autoantibodies in multiple sclerosis—from a simple idea to a complex concept. Nat. Rev. Neurol. 18[11]: 681-688) (Year: 2022).*

Wallukat (et al. 2012. The First Aptamer-Apheresis col. Specifically for Clearing Blood of B1-Receptor Autoantibodies—A Successful Proof of Principle Using Autoantibody-Positive SHR Rats. Circ. J. 76:2449-2455) (Year: 2012).*

Patel (and Hernandez. 2013. Targeting anti-beta-1-adrenergic receptor antibodies for dilated cardiomyopathy. Eur. J. Heart Fail. 15:724-729) (Year: 2013).*

Haberland A. et al., Circulation Research, 109(9) (2011), p. 986-992.

Haberland A. et al., Mol Cell Biochem, 393 (Apr. 2014), p. 177-180.

Prashat S. Patole et al., "G-Rich DNA Suppresses Systemic Lupus", the Journal of the American Society of Nephrology, vol. 16, pp. 3273-3280, 2005.

International Search Report dated Oct. 28, 2015 for PCT/EP2015/067951.

Searles, D.B., "Linguistic Approaches to Biological Sequences," Cabios, vol. 13, No. 4, pp. 333-344, 1997, XP002735332.

Searles, D.B., "The Language of Genes," Nature (London), vol. 420, No. 6912, Nov. 14, 2002, pp. 211-217, XP002735331, ISSN: 0028-0836.

Chiang, D., et al., "Grammatical Representations of Macromolecular Structure," Journal of Computational Biology, vol. 13, No. 5, Jan. 1, 2006, pp. 1077-1100, XP055165085.

Qi, L., et al., "RNACompress: Grammar-Based Compression and Informational Complexity Measurement of RNA Secondary Structure," BMC Bioinformatics, vol. 9, No. 1, Mar. 31, 2008, p. 176, XP021031746, ISSN: 1471-2105.

Wallukat, G., et al., "Agonistic Autoantibodies Directed Against G-Protein-Coupled Receptors and Their Relationship to Cardiovascular Diseases," Seminars in Immunopathology, vol. 36, No. 3, May 1, 2014, pp. 351-363, XP055165175, ISSN: 1863-2297, DOI: 10.1007/s00281-014-0425-9.

Wallukat, G., et al., "The first Aptamer-Apheresis Column Specifically for Clearing Blood of Beta1-Receptor Autoantibodies," Circulation Journal, vol. 76, No. 10, Oct. 2012, pp. 2449-2455, XP055165177, ISSN: 1346-9843, DOI: 10.1253/circj.CJ-12-0212.

Yao, Z., et al., CMfinder—A Covariance Model Based RNA Motif Finding Algorithm, Bioinformatics, vol. 22, No. 4, 2006, pp. 445-452, DOI: 10.1093/bioinformatics/btk008.

(56)                References Cited

OTHER PUBLICATIONS

Li, W., et al., "The EMBL-EBI Bioinformatics Web and Programmatic Tools Framework," Published online Apr. 6, 2015, W580-W584, Nucleic Acids Research, 2015, vol. 43, Web Server Issue doi: 10.1093/nar/gkv279.

Sorin, E.J., et al., "Does Water Play a Strutural Role in the Folding of Small Nucleic Acids?", Biophysical Journal, vol. 38, Apr. 2005, 2516-2524.

Santalucia, J., Jr., "A Unified View of Polymer, Dumbbell, and Oligonucleotide DNA Nearest-Neighbor Thermodynamics," Proc. Natl. Acad. Sci. USA, vol. 95, pp. 1460-1465, Feb. 1998, Biochemistry.

Sansom, C., "Database Searching with DNA and Protein Sequences: An Introduction," Copyright Henry Stewart Publications 1467-5463, Briefings in Bioinformatics, vol. 1, No. 1, 22-32, Feb. 2000.

Maio, Z., et al., "RNA-Puzzles Round II: Assessment of RNA Structure Prediction Programs Applied to Three Large RNA Structures, " Bioinformatics, RNA 21:1066-1084, Published by Cold Spring Harbor Laboratory Press for the RNA Society. 2015.

Zuker, M., "Mfold Web Server for Nucleic Acid Folding and Hybridization Prediction," 3406-3415, Nucleic Acids Research, 2003, vol. 31, No. 13, DOI: 10.1093/nar/gkg595.

Lorenz, R., et al., "2D Meets 4G: G-Quadruplexes in RNA Secondary Structure Prediction," IEEE/ACM Transactions on Computational Biology and Bioinformatics, vol. 10, No. 4, Jul./Aug. 2013.

Lorenz, R., et al., "ViennaRNA Package 2.0," AMB Algorithms for Molecular Biology 2011, 6:26, http://www.almob.org.content/6/1/26, copyright 2011.

Lassmann, T., et al., "Kalign2: High-Performance Multiple Alignment of Protein and Nucleotide Sequences Allowing External Features," Published online Dec. 22, 2008, 858-865, Nucleic Acids Research, 2009, vol. 37, No. 3, doi: 10.1093/nar/gkn1006.

Lassmann, T., et al., "Kalign—An Accurage and Fast Multiple Sequence Alignment Algorithm," BMC Bioinformatics 2005, 6:298, doi:10.1186/1471-2105-6-298.

Kladwang, W., et al., "Standardization of RNA Chemical Mapping Experiments," Biochemistry, ACS Publications, dx.dol.org/10.1021/bi5003426 Biochemistry 2014, 53, 3063-3065.

Anwar, M., et al., "Identification of Consensus RNA Secondary Structures Using Suffix Arrays," BMC Bioinformatics 2006, 7:244, doi: 10.1186/1471-2105-7-244.

Collingridge, P.W., et al., "MergeAlign: Improving Multiple Sequence Alighnment Performance by Dynamic Reconstruction of Consensus Multiple Sequence Alignments," BMC Bioinformatics, Collingridge and Kelly BMC Bioinformatics 2012, 13:117 http://www.biomedcentral.com/1471-2105/13/117.

Cruz, J.A., et al., "RNA-Puzzles: A CASP-Like Evaluation of RNA Three-Dimensional Structure Prediction," RNA (2012), 18:610-625, copyright 2012 RNA Society.

Carrillo, H., et al., "The Mutliple Sequence Alignment Problem in Biology," Siam J. Appl. Math. vol. 48, No. 5, Oct. 1988.

Tarmanci, A.O., "Efficient Pairwise RNA Structure Prediction Using Probabilistic Alignment Constraints in Dynalign," BMC Bioinformatics 2007, 8:130 doi:10.1186/1471-2105-8-130.

JP Office Action in Corresponding JP Application No. 2018-128622, mailed Jun. 28, 2022, 30 pages (English Translation).

Lee, et al., "Isolation of a Nuclease-resistant Decoy RNA That Selectively Blocks Autoantibody Binding to Insulin Receptors on Human Lymphocytes", J. Exp. Med., vol. 184, Aug. 1996, pp. 315-324.

Hwang, et al., "Prevention of passively transferred experimental autoimmune myasthenia gravis by an in vitro selected RNA aptamer", FEBS Letters, vol. 548, 2003, pp. 85-89.

Hughes, et al., "Principles of early drug discovery", British Journal of Pharmacology, vol. 162, 2011, pp. 1239-1249.

Ganson, et al., "Pre-existing anti-polyethylene glycol antibody linked to first-exposure allergic reactions to begnivacogin, a PEGylated RNA aptamer", J. Allergy Clin. Immunol., May 2016, 137(5), pp. 1610-1613.

DeAnda, Jr., et al., "Pilot Study of the Efficacy of a Thrombin Inhibitor for Use During Cardiopulmonary Bypass", Ann Thorac Surg, 1994, vol. 58, pp. 344-350.

Cyriac, et al., "Switch over from intravenous to oral therapy: A concise overview", Journal of Pharmacology and Pharmacotherapeutics, vol. 5, Apr.-Jun. 2014, Issue 2, pp. 83-87.

Vavalle, et al., "The REG1 anticoagulation system: a novel actively controlled factor IX inhibitor using RNA aptamer technology for treatment of acute coronary syndrome", Future Cardiol., May 2012, 8(3), pp. 371-382.

Ancellotti, et al., "Nucleotide-Derived Thrombin Inhibitors: A New Tool for an Old Issue", Cardiovascular & Hematological Agents in Medicinal Chemistry, 2009, vol. 7, pp. 19-28.

Lee SW, and Sullenger BA (1997) Isolation of a nuclease-resistant decoy RNA that can protect human acetylcholine receptors from myasthenic antibodies. Nat Biotechnol 15:41-45.

Wallace et al. (1997). Pharmacokinetics and Distribution of a 33P-labeled Anti-Human Immunodeficiency Virus Oligonucleotide (AR177) after Single- and Multiple-Dose Intravenous Administration to Rats. Journal of Pharmacology and Experimental Therapeutics. 280:1480-88.

Bates et al. (2009). Discovery and Development of the G-rich Oligonucleotide AS1411 as a Novel Treatment for Cancer. Exp Mol Pathol. 86(3):151-64.

Keefe et al. (2010). Aptamers as therapeutics. Nature Review 9:537-50.

European Medicines Evaluation Agency (2007). Pegaptanib/Macugen Scientific Discussion. EMEA 2-3.

Santosh B, and Yadava PK (2014) "Nucleic acid aptamers: research tools in disease diagnostics and therapeutics", Biomed Res Int, 2014, Article ID 540451; 13 pages.

Biochimie, "Loop residues of thrombin-binding DNA aptamer impact G-Quadruplex Stability and Thrombin Binding", 2011, vol. 93, No. 8, pp. 1231-1238.

JP Final Office Action in Corresponding JP Application No. 2020-174859, Mailed Jul. 26, 2022, 11 pages (English Translation).

* cited by examiner

| Sequence | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|---|
| 25 | 1 | 0.43 | 0.61 | 0.61 | 0.61 | 0.42 | 0.63 | 0.67 | 0.73 | 0.73 | 0.46 | 0.6 | 0.6 | 0.7 | 0.7 | 0.8 | 0.7 | 0.68 | 0.46 | 0.58 | 0.54 | 0.23 | 0.31 | 0.19 | 0.35 | 0.23 |
| 26 | | 1 | 0.81 | 0.44 | 0.72 | 0.46 | 0.47 | 0.53 | 0.47 | 0.47 | 0.46 | 0.52 | 0.52 | 0.6 | 0.6 | 0.5 | 0.5 | 0.52 | 0.57 | 0.46 | 0.46 | 0.33 | 0.24 | 0.33 | 0.36 | 0.31 |
| 27 | | | 1 | 0.17 | 0.6 | 0.67 | 0.47 | 0.53 | 0.53 | 0.6 | 0.67 | 0.78 | 0.61 | 0.6 | 0.6 | 0.6 | 0.5 | 0.56 | 0.61 | 0.61 | 0.67 | 0.28 | 0.28 | 0.33 | 0.28 | 0.31 |
| 28 | | | | 1 | 0.11 | 0.61 | 0.73 | 0.8 | 0.67 | 0.73 | 0.6 | 0.58 | 0.44 | 0.5 | 0.6 | 0.4 | 0.5 | 0.44 | 0.44 | 0.61 | 0.44 | 0.28 | 0.33 | 0.44 | 0.22 | 0.38 |
| 29 | | | | | 1 | 0.87 | 0.53 | 0.53 | 0.6 | 0.6 | 0.68 | 0.67 | 0.67 | 0.7 | 0.5 | 0.5 | 0.6 | 0.66 | 0.66 | 0.67 | 0.67 | 0.39 | 0.33 | 0.28 | 0.22 | 0.31 |
| 30 | | | | | | 1 | 0.6 | 0.67 | 0.8 | 0.87 | 0.62 | 0.65 | 0.52 | 0.6 | 0.7 | 0.7 | 0.7 | 0.5 | 0.28 | 0.59 | 0.66 | 0.21 | 0.1 | 0.25 | 0.35 | 0.36 |
| 31 | | | | | | | 1 | 0.6 | 0.67 | 0.63 | 0.6 | 0.53 | 0.63 | 0.6 | 0.4 | 0.4 | 0.6 | 0.47 | 0.47 | 0.53 | 0.4 | 0.33 | 0.2 | 0.33 | 0.33 | 0.36 |
| 32 | | | | | | | | 1 | 0.8 | 0.73 | 0.53 | 0.63 | 0.63 | 0.4 | 0.5 | 0.5 | 0.8 | 0.47 | 0.4 | 0.47 | 0.4 | 0.33 | 0.2 | 0.53 | 0.33 | 0.31 |
| 33 | | | | | | | | | 1 | 0.6 | 0.67 | 0.87 | 0.87 | 0.67 | 0.5 | 0.4 | 0.5 | 0.5 | 0.6 | 0.53 | 0.6 | 0.63 | 0.4 | 0.27 | 0.4 | 0.53 | 0.38 |
| 34 | | | | | | | | | | 1 | 0.87 | 0.6 | 0.67 | 0.6 | 0.4 | 0.6 | 0.5 | 0.6 | 0.6 | 0.67 | 0.6 | 0.27 | 0.33 | 0.4 | 0.33 | 0.33 |
| 35 | | | | | | | | | | | 1 | 0.7 | 0.58 | 0.7 | 0.7 | 0.7 | 0.8 | 0.8 | 0.89 | 0.51 | 0.54 | 0.34 | 0.46 | 0.32 | 0.35 | 0.36 |
| 36 | | | | | | | | | | | | 1 | 0.37 | 0.6 | 0.5 | 0.5 | 0.6 | 0.6 | 0.46 | 0.89 | 0.56 | 0.46 | 0.28 | 0.46 | 0.25 | 0.46 | 0.36 |
| 37 | | | | | | | | | | | | | 1 | 0.7 | 0.7 | 0.7 | 0.8 | 0.64 | 0.59 | 0.51 | 0.46 | 0.31 | 0.53 | 0.32 | 0.4 | 0.36 |
| 38 | | | | | | | | | | | | | | 1 | 0.8 | 0.7 | 0.8 | 0.9 | 0.6 | 0.9 | 0.7 | 0.4 | 0.3 | 0.4 | 0.4 | 0.3 |
| 39 | | | | | | | | | | | | | | | 1 | 0.8 | 0.7 | 0.8 | 0.6 | 0.8 | 0.7 | 0.3 | 0.3 | 0.6 | 0.4 | 0.3 |
| 40 | | | | | | | | | | | | | | | | 1 | 0.9 | 0.8 | 0.8 | 0.8 | 0.6 | 0.3 | 0.3 | 0.5 | 0.4 | 0.2 |
| 41 | | | | | | | | | | | | | | | | | 1 | 0.7 | 0.5 | 0.7 | 0.8 | 0.3 | 0.3 | 0.4 | 0.5 | 0.5 |
| 42 | | | | | | | | | | | | | | | | | | 1 | 0.82 | 0.69 | 0.62 | 0.19 | 0.27 | 0.31 | 0.3 | 0.15 |
| 43 | | | | | | | | | | | | | | | | | | | 1 | 0.66 | 0.58 | 0.28 | 0.38 | 0.14 | 0.35 | 0.23 |
| 44 | | | | | | | | | | | | | | | | | | | | 1 | 0.34 | 0.23 | 0.34 | 0.21 | 0.3 | 0.23 |
| 45 | | | | | | | | | | | | | | | | | | | | | 1 | 0.26 | 0.38 | 0.21 | 0.26 | 0.16 |
| 46 | | | | | | | | | | | | | | | | | | | | | | 1 | 0.46 | 0.43 | 0.4 | 0.68 |
| 47 | | | | | | | | | | | | | | | | | | | | | | | 1 | 0.21 | 0.3 | 0.46 |
| 48 | | | | | | | | | | | | | | | | | | | | | | | | 1 | 0.46 | 0.46 |
| 49 | | | | | | | | | | | | | | | | | | | | | | | | | 1 | 0.36 |
| 50 | | | | | | | | | | | | | | | | | | | | | | | | | | 1 |

APTAMERS FOR USE AGAINST AUTOANTIBODY-ASSOCIATED DISEASES

CROSS-REFERENCE TO RELATED APPLICATION

This application is a § 371 national stage entry of International Application No. PCT/EP2015/067951 filed Aug. 4, 2015, which claims priority to and the benefit of European Application No. 14179715.9 filed Aug. 4, 2014, both of which are hereby incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 31, 2017, is named 103-4 (157741_00201) _SL.txt and is 19,397 bytes in size.

TECHNICAL FIELD

The present invention relates to new aptamer molecules for use in the treatment and/or diagnosis of autoimmune diseases associated with autoantibodies against G-protein coupled receptors, a pharmaceutical composition comprising such aptamer molecules, an apheresis column comprising such aptamer molecules and a method for the determination of nucleotide sequences for use as sequences of aptamer molecules.

BACKGROUND OF THE INVENTION

The immune system forms an essential part of every mammalian. Mammals make use of its immune system in the defense against microorganisms, in detection and removal of aberrant cells like e.g. tumor cells, and in regeneration of tissue. Thereby, the organism relies on two interconnected defense mechanisms, humoral and cellular immunity.

Antibodies, when bound to their antigen are triggers of the humoral immune response. Antibodies can act in multiple ways. Apart from neutralization of the antigen, antibodies also activate the complement system. There are also antibodies which are directed to antigens of the own body. As reason for the generation of these so-called autoantibodies, molecular mimikry and/or bystander activation are seen. Specific binding of the autoantibodies to own antigens can activate natural killer cells (NK cells) which are able to facilitate degradation of these antigens.

Autoimmune diseases are based on such specific recognition and binding of antibodies directed to own constituent parts of the body which triggers an immune response against own cells or tissues. Apart from this immunostimulatory effect, autoantibodies can contribute to the development of pathogenic phenotypes also by other mechanisms.

It is well known that there are autoantibodies which are specific for the extracellular part of G-protein coupled receptors such as: adrenergic alpha-1 receptor, adrenergic beta-1 receptor, adrenergic beta-2 receptor, endothelin1 ETA receptor, muscarinic M2 receptor, angiotensin II AT1 receptor, proteinase activated receptors (PAR) receptors, MAS-receptors, 5HT4-receptors and/or M3-receptors and, upon specific binding, can activate or block these receptors.

G-protein coupled receptors are signal transduction molecules which transduce information from the extracellular space into the cell. They belong to a receptor family which covers more than 1000 different receptors and is subdivided in five subgroups. They represent a principle of signal transduction over the cell membrane into the cell which is present in many different species.

A typical property of GPCRs is that they have three different extracellular loops with different epitopes to which substances may bind and cause different intracellular reactions. The humoral protein adrenaline is able to bind to the adrenergic beta-1 receptor to increase the strength and frequency of the beat of a heart muscle cell.

Functionally pathogenic autoantibodies against GPCRs are frequently but not always of the subtype IgG3 (glycoprotein Immunoglobulin G, subclass 3) and have the ability to bind to different GPCR loops and to different places inside of the loops. These functionally pathogenic antibodies exert a pathological cellular and in turn organic function by their interaction with the GPCR.

Thus, there are many different autoantibodies which are directed against different receptors. In case of the heart muscle, these are e.g. the autoantibodies directed against the adrenergic beta-1 receptor or the muscarinic acetylcholine receptor. Other antibodies which have an important role in other diseases are directed against the adrenergic alpha-1 receptor, adrenergic alpha-2 receptor, adrenergic beta-2 receptor, endothelin1 ETA receptor, muscarinic M2 receptor, angiotensin II AT1 receptor, proteinase activated receptors (PAR) receptors, MAS-receptors, 5HT4-receptors, M3-receptors and others.

The presence of such autoantibodies in an organism can lead to agonistic or antagonistic effects in the sense of a permanent activation or blockade of the respective receptors which play a role in the development of the disease.

Dilated cardiomyopathy (DCM) is one of the diseases in which a high percentage of the patients have such activating autoantibodies binding to extracellular parts of the adrenergic beta-1 receptor, in particular to the 1st or 2nd loop of adrenergic beta-1 receptor. Consequently, an autoimmune pathogenesis of DCM in these patients was suggested. Upon binding of these autoantibodies the receptors are continuously activated because the physiologic feedback mechanism which limits the activation of the GPCRs is suppressed.

There are other diseases of the cardiovascular system which were suggested to be in relation to the presence of autoantibodies against G-protein coupled receptors such as, Chagas' cardiomyopathy, peripartum cardiomyopathy, myocarditis, pulmonary hypertension and malignant hypertension. Autoantibodies against G-protein coupled receptors were also found in patients e.g. with glaucoma, Diabetes mellitus, benign prostatic hyperplasia, scleroderma, Raynaud syndrome, and pre-eclamsia and in chronic Chagas' disease as well as those with kidney allograft rejection.

Usually, the epitope regions of these receptors consist of peptide chains comprising about 20 amino acids, while the disease-specific epitopes constitute a sequence of 3 to 5 amino acids of one of these regions. However, undesired interaction of autoantibodies with these epitopes plays an important role for the development and chronification of several autoimmune diseases.

In recent studies, it could be shown that removal of these autoantibodies from the blood via immunoglobulin adsorption contributes to regeneration of the heart muscle (Wallukat G, Reinke P, Dorffel W V, Luther H P, Bestvater K, Felix S B, Baumann G. (1996) *Removal of autoantibodies in dilated cardiomyopathy by immunoadsorption.* Int J Cardiol. 54:191-195; Müller J, Wallukat G, Dandel M, Bieda H, Brandes K, Spiegelsberger S, Nissen E, Kunze R, Hetzer R (2000) *Immunoglobulin adsorption in patients with idiopathic dilated cardiomyopathy.* Circulation. 101:385-391. W. V. Dorffel, S. B. Felix, G. Wallukat, S. Brehme, K. Bestvater, T. Hofmann, F. K. Kleber, G. Baumann, P. Reinke (1997) Short-term hemodynamic effects of immunoadsorption in dilated cardiomyopathy. Circulation 95, 1994-1997 and W. V. Dorffel, G. Wallukat, Y. Dorffel, S. B. Felix, G. Baumann (2004) Immunoadsorption in idiopathic dilated cardiomyopathy, a 3-year follow-up. Int J. Cardiol. 97,20 529-534).

It has further been found that certain aptamers can be used to interfere with the interaction of antibodies, in particular of autoantibodies, specific for the 2nd extracellular loop of human beta-1-adrenergic receptor with its target (WO 2012/000889 A1). Aptamers are short-chain oligonucleotides characterized by a high affinity to their target molecule. By inhibiting the interaction, the aptamers were able to diminish or even abolish the permanent activation of the beta-1-adrenergic receptor without the need for removal of these antibodies. Further aptamers for the use in treatment and/or diagnosis of autoimmune diseases that are associated with the presence of autoantibodies against G-protein coupled receptors have been disclosed in WO 2012/119938 A2.

According to one preferred embodiment, the aptamers are used to diminish or abolish the activation of the G-protein coupled receptor by the respective autoantibody. According to another preferred embodiment, the aptamers are used to neutralize the autoantibodies directed against a G-protein coupled receptor and/or to reduce the effect of the autoantibodies on the G-protein coupled receptors that they are directed against.

However, only a very limited number of aptamers which could be applied against the specific above-named autoimmune diseases is available at present and their effectiveness and harmlessness for the application in human patients remains to be confirmed. The availability of additional aptamers which show enhanced interference with the interaction of autoantibodies with GPCRs is therefore desired.

Accordingly, it is an object of the present invention to provide new aptamers for the use in the treatment and/or diagnosis of autoimmune diseases associated with autoantibodies against G-protein coupled receptors.

Furthermore, it is another object of the present invention to provide a pharmaceutical composition comprising such aptamer molecules as well as apheresis columns comprising such aptamers.

It is also an object of the present invention to provide a method for the determination of nucleotide sequences of new aptamers for the use in the therapy and/or diagnosis of autoimmune diseases associated with autoantibodies against G-protein coupled receptors.

SUMMARY OF THE INVENTION

This object is solved by the aspects of the present invention as specified hereinafter.

According to the first aspect of the present invention, an aptamer is provided comprising a nucleotide sequence which satisfies a grammar defined by the set of production rules P:

4

$P = \{$ $$
\begin{array}{lll}
S & \to & M\,|\,Y\,|\,D\,|\,E\,|\,H & (1) \\
M & \to & NRM & (2) \\
M & \to & MR & (3) \\
M & \to & RM & (4) \\
N & \to & M & (5) \\
D & \to & YM & (6) \\
E & \to & VM & (6a) \\
Y & \to & K\,|\,KL\,|\,LK\,|\,LKL & (7) \\
H & \to & LV\,|\,V & (8) \\
R & \to & L & (9) \\
Z & \to & A\,|\,C\,|\,G\,|\,T & (10) \\
L & \to & ZL\,|\,Z & (11) \\
BX & \to & G^x & (12) \\
CX & \to & BXLBX & (13) \\
M & \to & CXLCX & (14) \\
K & \to & CXLBX & (15) \\
V & \to & CXL & (16) \\
\end{array}
$$

$\}$ with the conditions
a.) Q is the set of natural numbers
b.) F is a subset of natural numbers defined as $$F := \{X \in Q | (X > 1)\}$$

c.) Using F we define:

$$
\begin{array}{ll}
\forall\,X \in F\,\exists\,M{:}M \to CXLCX & (1) \\
\forall\,X \in F\,\exists\,K{:}K \to CXLBX & (2) \\
\forall\,X \in F\,\exists\,V{:}V \to CXL & (3) \\
\forall\,X \in F{:}CX \to BXLBX & (4) \\
\forall\,X \in F{:}BX \to \displaystyle\prod_{1}^{X} G & (5) \\
\end{array}
$$

d.) U is a set of non-terminals defined as

U={S, M, N, D, E, Y, H, R, Z, L, BX, CX, K, V}

For BX and CX see c)
e.) W is a set of terminals defined as

W={A, C, G, T, $G^x$}

$G^X$ denotes all terminals which can be derived according to b.) and c.)(5)
f.) S ∈ U is the starting symbol
for use in the treatment and/or diagnosis of autoimmune diseases associated with autoantibodies against G-protein coupled receptors, wherein "A" means an adenine nucleotide, "C" means a cytosine nucleotide, "G" means a guanine nucleotide and "T" means a thymine nucleotide if the nucleotide sequence is a DNA sequence, and "T" means a uracil nucleotide if the nucleotide sequence is a RNA sequence, wherein the aptamer does not comprise the nucleotide sequence GGTTGGTGTGGTTGG (SEQ ID No:

US 12,630,828 B2

5

22), GGTTGGTGTGGT (SEQ ID NO: 23) or
CGCCTAGGTTGGGTAGGGTGGTGGCG (SEQ ID No:
24).

In a preferred embodiment of the first aspect of the
invention, the nucleotide sequence of the aptamer has a
length of at most 593 nucleotides.

In another preferred embodiment of the first aspect of the
invention, the nucleotide sequence is a DNA sequence.

In yet another preferred embodiment of the first aspect of
the invention, the nucleotide sequence is a RNA sequence.

In a preferred embodiment of the first aspect of the
invention, the nucleotide sequence comprised in the aptamer
is any one of the following sequences:

(5'-GTTGTTTGGGGTGG-3' SEQ ID No: 1), (5'-GTTGTTTGGGGTGGT-3' SEQ ID No: 2)

(5'-GGTTGGGGTGGGTGGGGTGGGTGGG-3' SEQ ID No: 3), (5'-TTTGGTGGTGGTGGTTGTGGTGGTGGTG-3' SEQ ID No: 4), (5'-TTTGGTGGTGGTGGTTGTGGTGGTGGTGG-3' SEQ ID No: 5), (5'-TTTGGTGGTGGTGGTTTTGGTGGTGGTGG-3' SEQ ID No: 6), (5'-TTTGGTGGTGGTGGTGGTGGTGGTGGTG-3' SEQ ID No: 7), (5'-TTTGGTGGTGGTGGTTTGGGTGGTGGTGG-3' SEQ ID No: 8), (5'-TGGTGGTGGTGGT-3' SEQ ID No: 9), (5'-GGTGGTGGTGG-3' SEQ ID No: 10), (5'-GGTGGTTGTGGTGG-3' SEQ ID No: 11), (5'-GGTGGTGGTGGTTGTGGTGGTGGTGG-3' SEQ ID No: 12), (5'-GGTGGTGGTGGTTGTGGTGGTGGTGGTTGTGGTGGTGGTGGTTGTG
GTGGTGGTGG-3' SEQ ID No: 13), (5'-GGTGGTTGTGGTGGTTGTGGTGGTTGTGGTGG-3' SEQ ID
No: 14), (5'-TTTGGTGGTGGTGGTTGTGGTGGTGGTGGTTT-3' SEQ ID
No: 15), (5'-GGTGGTGGTGTTGTGGTGGTGGTGGTTT-3' SEQ ID No: 16), (5'-TTTGGTGGTGGTGGTGTGGTGGTGGTGG-3' SEQ ID No: 17), (5'-TGGTGGTGGT-3' SEQ ID No: 18), (5'-TTAGGGTTAGGGTTAGGGTTAGGG-3' SEQ ID NO: 20),

In a preferred embodiment of the first aspect of the
invention, the nucleotide sequence of the aptamer has a
length of at least 4 nucleotides, preferably at least 8 nucleo-
tides, more preferably at least 12 nucleotides.

In a preferred embodiment of the first aspect of the
invention, the nucleotide sequence of the aptamer has a
length of at most 120 nucleotides, preferably at most 100
nucleotides, more preferably at most 80 nucleotides.

In a preferred embodiment of the first aspect of the
invention, the aptamer is able to interact with an autoanti-
body, preferably an autoantibody which is specific for a
G-protein coupled receptor, preferably specific for any one
of the human G-protein coupled receptor adrenergic alpha-1
receptor, adrenergic beta-1 receptor, adrenergic beta-2
receptor, endothelin 1 ETA receptor, muscarinic M receptor,
angiotensin II AT1 receptor, PAR receptors, MAS-receptor,
5HT4-receptor and/or M3 receptor.

In a preferred embodiment of the first aspect of the
invention, the aptamer is for use as selective ingredient during therapeutic apheresis of blood or constituents thereof
of a patient suffering from an autoimmune disease associ-
ated with the occurrence of autoantibodies against G-protein
coupled receptors.

In a preferred embodiment of the first aspect of the
invention, the autoimmune disease is one of cardiomyopa-
thy, ischemic cardiomyopathy (iCM), dilated cardiomyopa-
thy (DCM), peripartum cardiomyopathy (PPCM), idiopathic
cardiomyopathy, Chagas' cardiomyopathy, chemotherapy-
induced cardiomyopathy, Chagas' megacolon, Chagas'
megaesophagus, Chagas' neuropathy, benign prostatic
hyperplasia, scleroderma, Raynaud syndrome, peripheral
artery occlusive disease (PAOD), pre-eclamsia, kidney
allograft rejection, myocarditis, glaucoma, hypertension,
pulmonary hypertension, malignant hypertension, metabolic
syndrome, Alopecia, Alopecia areata, migraine, Parkinson's
disease, epilepsia, cluster headache, multiple sclerosis,
depression, regional pain syndrome, instable angina pecto-
ris, systemic lupus erythematosus (SLE), schizophrenia,
Sjögren's syndrome, periodontitis, atrial fibrillation, vitiligo,
hemolytic uremic syndrome, stiff person syndrome, and/or
congenital heart block.

In a preferred embodiment of the first aspect of the
invention, the aptamer is for use in in vitro detection of an
antibody being specific for a G-protein coupled receptor,
preferably the human G-protein coupled receptor adrenergic
alpha-1 receptor, adrenergic beta-1 receptor, adrenergic
beta-2 receptor, endothelin 1 ETA receptor, muscarinic M
receptor, angiotensin II AT1 receptor, PAR receptors, MAS-
receptor, 5HT4-receptor and/or M3 receptor.

In another preferred embodiment of the first aspect of the
invention, the antibody to be detected is an autoantibody.

In yet another preferred embodiment of the first aspect of
the invention, the antibody is present in or derived from a
body fluid, preferably a fluid of a human body, more
preferably of human blood, plasma, serum, urine, feces,
synovial fluid, interstitial fluid, lymph, saliva, spinal fluid
and/or lacrimal fluid.

In yet another preferred embodiment of the first aspect of
the invention, the body fluid is taken from an individual
suffering from or suspected to suffer from an autoimmune
disease, preferably an autoimmune disease associated with
presence in the serum of the patient of autoantibodies
specific for a G protein coupled receptor, more preferably
autoimmune diseases associated with presence in the serum
of the patient of autoantibodies specific for adrenergic
alpha-1 receptor, adrenergic beta-1 receptor, adrenergic
beta-2 receptor, endothelin 1 ETA receptor, muscarinic M
receptor, angiotensin II AT1 receptor, PAR receptors, MAS-
receptor, 5HT4-receptor and/or M3 receptor.

In yet another preferred embodiment of the first aspect of
the invention, the aptamer comprises the following nucleo-
tide sequence (5'-
GGTGGTGGTGGTTGTGGTGGTGGTGG-3' SEQ ID No.
12).

According to the second aspect of the present invention,
a pharmaceutical composition is provided comprising at
least one aptamer of the present invention and, optionally, at
least one pharmaceutically acceptable excipient.

In a preferred embodiment of the second aspect of the
present invention, the pharmaceutical composition is pro-
vided for the use in the treatment of autoimmune diseases
associated with autoantibodies against G-protein coupled
receptors.

According to the third aspect of the present invention, an
apheresis column comprising an aptamer according to the
first aspect of the invention is provided.

In a preferred embodiment of the third aspect of the present invention, the apheresis column is provided for use in treatment and/or diagnosis of an autoimmune disease, wherein the autoimmune disease is cardiomyopathy, dilated cardiomyopathy (DCM), ischemic cardiomyopathy (iCM), peripartum cardiomyopathy (PPCM), idiopathic cardiomyopathy, Chagas' cardiomyopathy, chemotherapy-induced cardiomyopathy, Chagas' megacolon, Chagas' megaesophagus, Chagas' neuropathy, benign prostatic hyperplasia, scleroderma, Raynaud syndrome, peripheral artery occlusive disease (PAOD), pre-eclamsia, kidney allograft rejection, myocarditis, glaucoma, hypertension, pulmonary hypertension, malignant hypertension, metabolic syndrome, Alopecia, Alopecia areata, migraine, Parkinson's disease, epilepsia, cluster headache, multiple sclerosis, depression, regional pain syndrome, instable angina pectoris, systemic lupus erythematosus (SLE), schizophrenia, Sjögren's syndrome, periodontitis, atrial fibrillation, vitiligo, hemolytic uremic syndrome, stiff person syndrome, and/or congenital heart block.

According to the fourth aspect of the present invention, a method for the preparation of an aptamer oligonucleotide is provided comprising the steps of determination of a nucleotide sequence for use as an aptamer sequence comprising the application of the following set of production rules P:

$$P = \{$$

| | | | |
|---|---|---|---|
| $S$ | $\rightarrow$ | $M \mid Y \mid D \mid E \mid H$ | (1) |
| $M$ | $\rightarrow$ | $NRM$ | (2) |
| $M$ | $\rightarrow$ | $MR$ | (3) |
| $M$ | $\rightarrow$ | $RM$ | (4) |
| $N$ | $\rightarrow$ | $M$ | (5) |
| $D$ | $\rightarrow$ | $YM$ | (6) |
| $E$ | $\rightarrow$ | $VM$ | (6a) |
| $Y$ | $\rightarrow$ | $K \mid KL \mid LK \mid LKL$ | (7) |
| $H$ | $\rightarrow$ | $LV \mid V$ | (8) |
| $R$ | $\rightarrow$ | $L$ | (9) |
| $Z$ | $\rightarrow$ | $A \mid C \mid G \mid T$ | (10) |
| $L$ | $\rightarrow$ | $ZL \mid Z$ | (11) |
| $BX$ | $\rightarrow$ | $G^x$ | (12) |
| $CX$ | $\rightarrow$ | $BXLBX$ | (13) |
| $M$ | $\rightarrow$ | $CXLCX$ | (14) |
| $K$ | $\rightarrow$ | $CXLBX$ | (15) |
| $V$ | $\rightarrow$ | $CXL$ | (16) |

$$\}$$

with the conditions a.) Q is the set of natural numbers b.) F is a subset of natural numbers defined as $$F := \{X \in Q | (X > 1)\}$$

c.) Using F we define:

$$\forall\, X \in F \,\exists\, M : M \rightarrow CXLCX \tag{1}$$

$$\forall\, X \in F \,\exists\, K : K \rightarrow CXLBX \tag{2}$$

$$\forall\, X \in F \,\exists\, V : V \rightarrow CXL \tag{3}$$

$$\forall\, X \in F : CX \rightarrow BXLBX \tag{4}$$

$$\forall\, X \in F : BX \rightarrow \prod_{1}^{X} G \tag{5}$$

d.) U is a set of non-terminals defined as

U={S, M, N, D, E, Y, H, R, Z, L, BX, CX, K, V}

For BX and CX see c)

e.) W is a set of non-terminals defined as

W={A, C, G, T, $G_x$}

$G^x$ denotes all terminals which can be derived according to b.) and c.)(5)

f.) S ∈ U is the starting symbol wherein "A" means an adenine nucleotide, "C" means a cytosine nucleotide, "G" means a guanine nucleotide and "T" means a thymine nucleotide if the nucleotide sequence is a DNA sequence, and "T" means a uracil nucleotide if the nucleotide sequence is a RNA sequence, and producing an aptamer oligonucleotide having the nucleotide sequence obtained in the first step.

DESCRIPTION OF FIGURES

FIG. 9 shows mutual sequence identities of aptamers calculated using the given grammar according to the invention with each other (SEQ ID No.: 25 to 45) and with control sequences (SEQ ID No.: 46 to 50) not according to the invention.

DETAILED DESCRIPTION OF THE INVENTION

Figure 1:
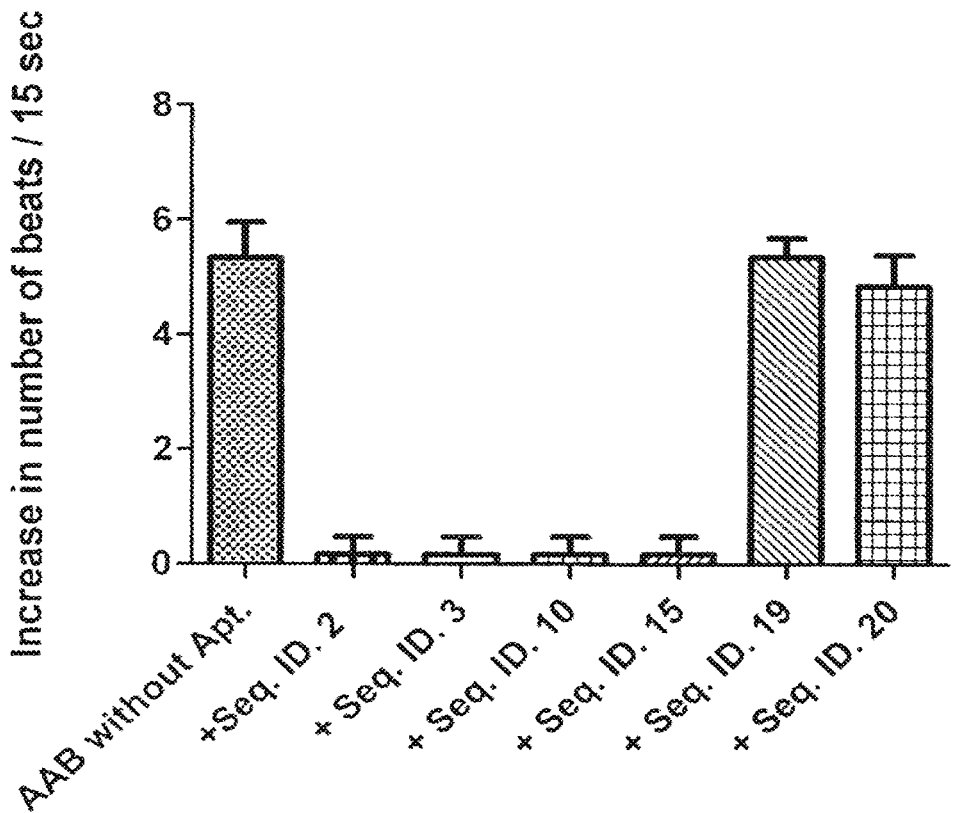
FIG. 1 shows the neutralization of the alpha1 adrenoceptor AABs by aptamers (2 µl).

The present inventors recognised that oligonucleotides which are able to interact with autoantibodies specific for G-protein coupled receptors and interfere with the pathogenic interaction between these two molecules share defined molecular patterns. Departing from this recognition, the inventors successfully devised a grammar defined by the set of production rules P according to claim 1 reproducing the structural patterns of aptamers which are effective binders to GPCR-autoantibodies.

Heretofore, only a very limited number of aptamers was known in the art which appear to interfere with the binding of autoantibodies to G-protein coupled receptors. The attempt to identify new aptamers which are suitable for the treatment and/or diagnosis of autoimmune diseases associated with autoantibodies against G-protein coupled receptors is very laborious and is anything but promising to finally determine a suitable nucleotide sequence, in particular in view of the strict requirements for the pharmaceutical application of aptamers in diagnosis or therapy in human patients. To this end, it was highly desired to provide additional aptamers for use against these autoimmune diseases.

The present inventors now identified for the first time the structural commonalities of aptamers which are effective against diseases associated with G-protein coupled receptor autoantibodies and were able to define a set of production rules to define a set of nucleotide sequences which are functional and effective as aptamers. Thus, it now became possible for the first time to provide an increased number of aptamers interfering with GPCR-autoantibodies.

A common approach to identify sequences sharing the same or nearly highly identical properties is to filter all those sequences showing a sequence identity of e.g. at least 80 or 90% to a given sequence having such properties. The idea behind such an approach is that highly similar sequences should share highly similar properties.

This relationship between sequence similarity and preservation of functional properties has been used and applied for many years for instance in the context of knowledge based modeling. However, it is known that there are nucleotide or amino acid sequences sharing low mutual sequence identities but still have highly similar properties. To recognize and describe those sequences which retain the function in spite of low sequence similarity, more sophisticated methods are needed.

The inventors' recognition presented herein is to develop and use a grammar to specifically recognize and define valid and functional sequences without consideration of sequence identities. Using this grammar, it is possible to calculate only sequences having the specific, sought-after sequence properties. The same grammar can also be used to specifically recognize sequences which have the desired property in a pool of arbitrary sequences.

The accuracy of grammars in general is reflected by the fact that only one wrong character or a character at a wrong position may lead to a sequence that cannot be recognized by the grammar. This is highly relevant for the present invention and its application. One wrong nucleotide at a crucial position of the claimed aptamer sequences and the sequences may not be recognized by the grammar.

Using this approach, the invention allows to specifically exclude all sequences which do not meet the sequence criteria set by the grammar and would thus lead to an inability to bind GPCR autoantibodies. On the other hand, this method allows calculating and/or filtering all sequences which meet the set criteria regardless of any complexity or sequence identity to a given template.

In order to demonstrate that the functional properties of the calculated sequences is not a function of a sequence identity or similarity but of the grammar (functional sequences with low mutual sequence identities have equal or highly similar properties), the rules of the given grammar are applied with consideration of the boundary conditions to calculate several sequences showing low mutual sequence identities. Nevertheless, it will be demonstrated herein that all sequences thus produced by the grammar have the claimed properties of binding to GPCR autoantibodies.

FIG. 9 shows the IDs (SEQ ID No.: 25 to 45) of the calculated aptamers according to the invention and their mutual sequence identities. Sequence identities have been determined by using the Kalign software with open penalty and extension penalty values set to maximum. This software has been described in Lassmann and Sonnhammer, Kalign— an accurate and fast multiple sequence alignment algorithm. (2005) BMC bioinformatics 6 :298, Lassmann et al., Kalign2: high-performance multiple alignment of protein and nucleotide sequences allowing external features. (2009 February) Nucleic acids research 37 (3):858-65, Goujon et al., A new bioinformatics analysis tools framework at EMBL-EBI. (2010 July) Nucleic acids research 38 (Web Server issue): W695-9, McWilliam et al., Analysis Tool Web Services from the EMBL-EBI. (2013 July) Nucleic acids research 41 (Web Server issue): W597-600 and Li et al., The EMBL-EBI bioinformatics web and programmatic tools framework. (2015 Jul. 1) Nucleic acids research 43 (W1): W580-4.

According to one embodiment of the present invention, identities between two nucleotide sequences may be determined as laid out above. According to another embodiment of the present invention, identities between two nucleotide sequences may be determined according to one or more of the documents cited above.

A broad range of different claimed sequences according to the invention has been calculated essentially covering the complete range of theoretically possible sequence identities. It can be seen from FIG. 9 that the mutual sequence identities among functional aptamer sequences range from 90% (between SEQ ID No.: 38 and 42 or 40 and 41) to 11% (between SEQ ID No.: 28 and 29).

All sequences may be calculated and/or are recognized by the given rules of the grammar using a Shift-Reduce Parser as shown below for sequences SEQ ID No: 12, 3, 10 and 15.

Randomized oligonucleotides which are not according to the invention have been used as control sequences (SEQ ID No.: 46 to 50). These sequences are not recognized by the given grammar. The controls show a sequence identity to the functional inventive aptamers in a range of 10% (between SEQ ID No.: 30 and 47) to 60% (between SEQ ID No.: 39 and 48).

Figure 10:
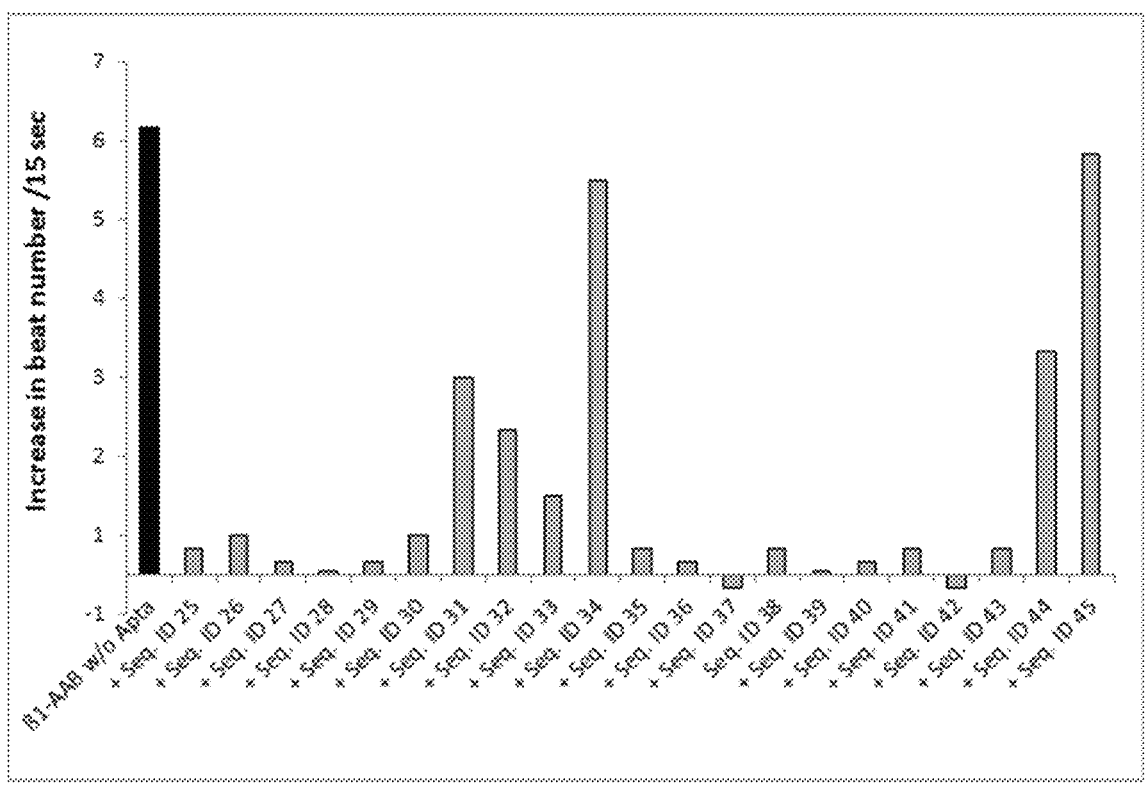
FIG. 10 shows the neutralization of the beta1 adrenoceptor AABs by 100 nM of different aptamers (SEQ ID No.: 25 to 45) according to the invention (2 µl).
Figure 11:
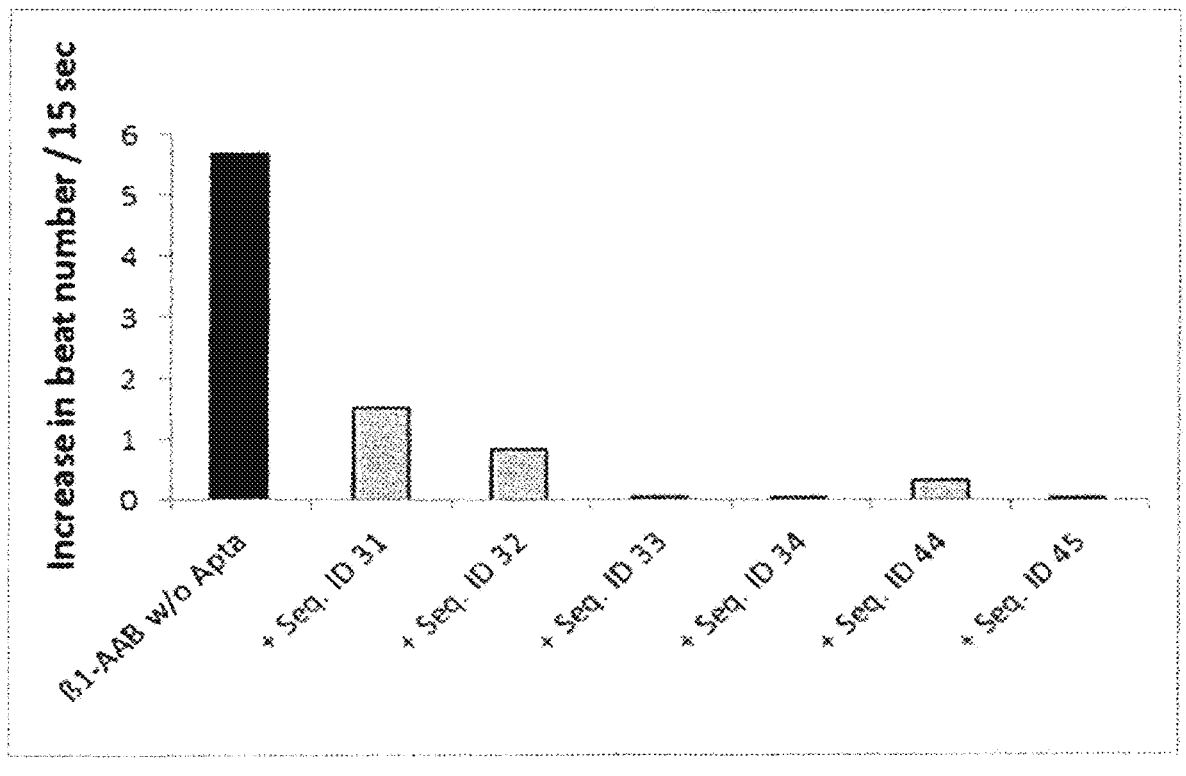
FIG. 11 shows the neutralization of the beta1 adrenoceptor AABs by 400 nM of different aptamers (SEQ ID No.: 31 to 34, 44 and 45) according to the invention (2 µl).
Figure 12:
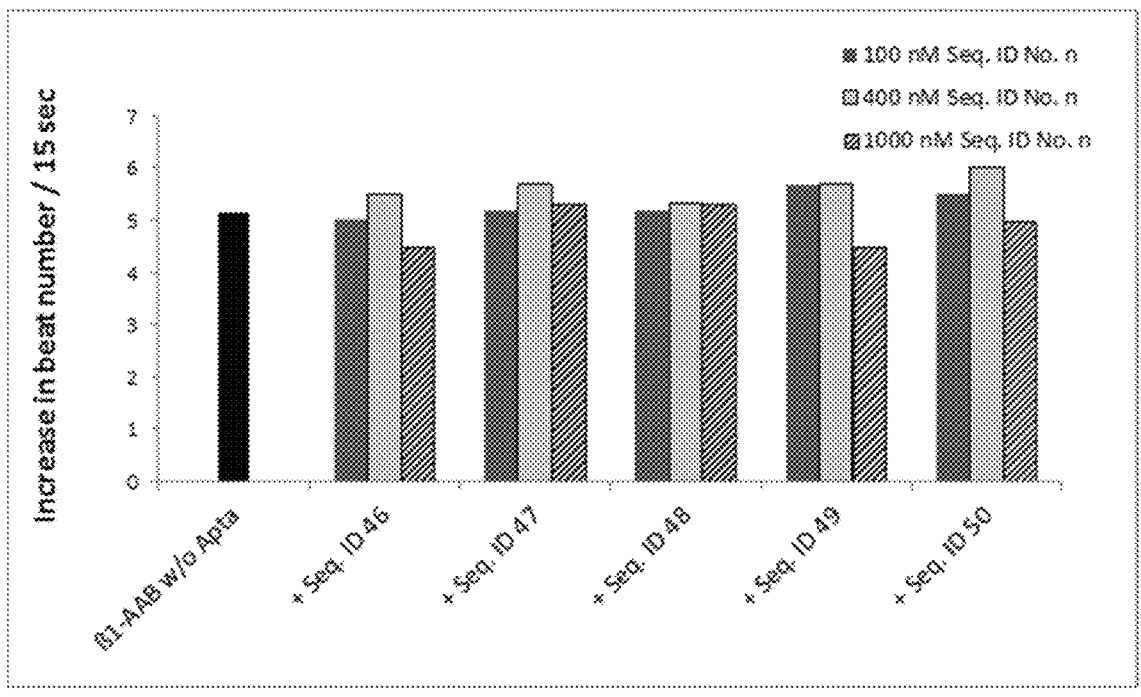
FIG. 12 shows the neutralization of the beta1 adrenoceptor AABs by 100 nM, 400 nM and 1000 nM of different control sequences (SEQ ID No.: 46 to 50) not according to the invention (2 µl).
Figure 13:
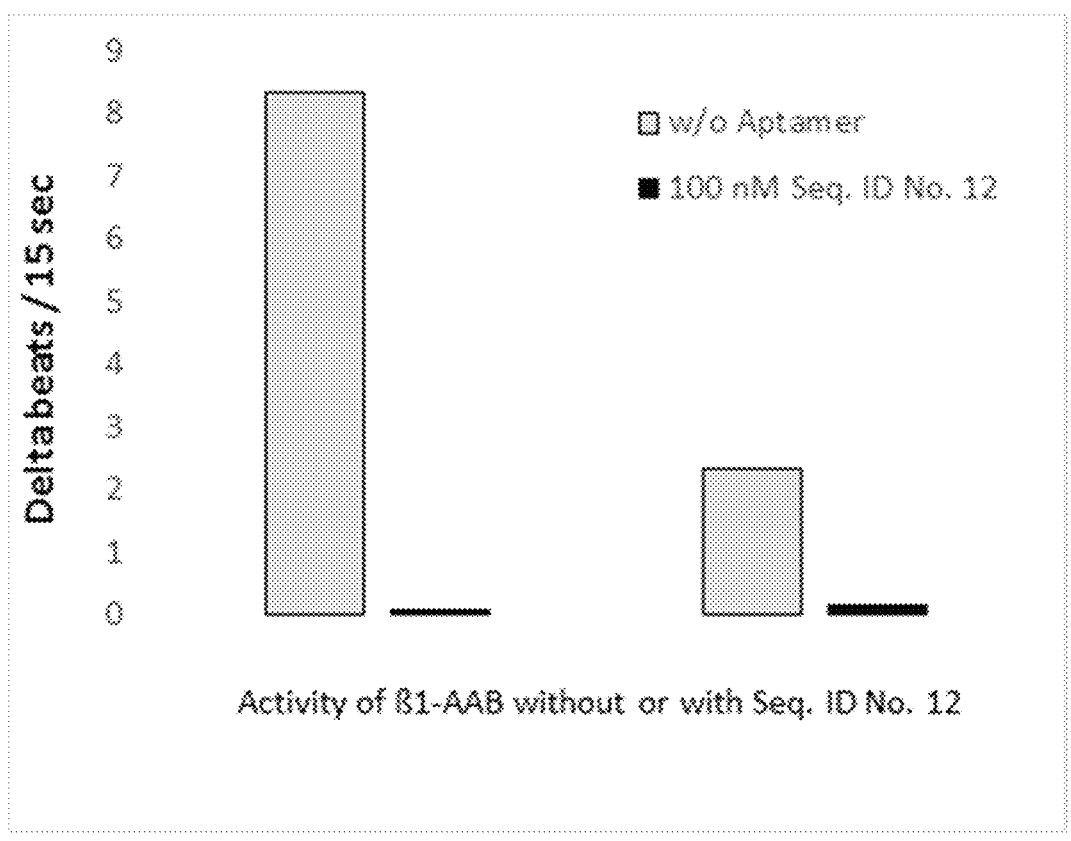
FIG. 13 shows the activity of beta 1 adrenoceptor AABs isolated from patients suffering from depression or Chagas' cardiomyopathy (from left to right) in the absence or presence of 100 nM of the inventive aptamer of SEQ ID No.: 12.
Figure 14:
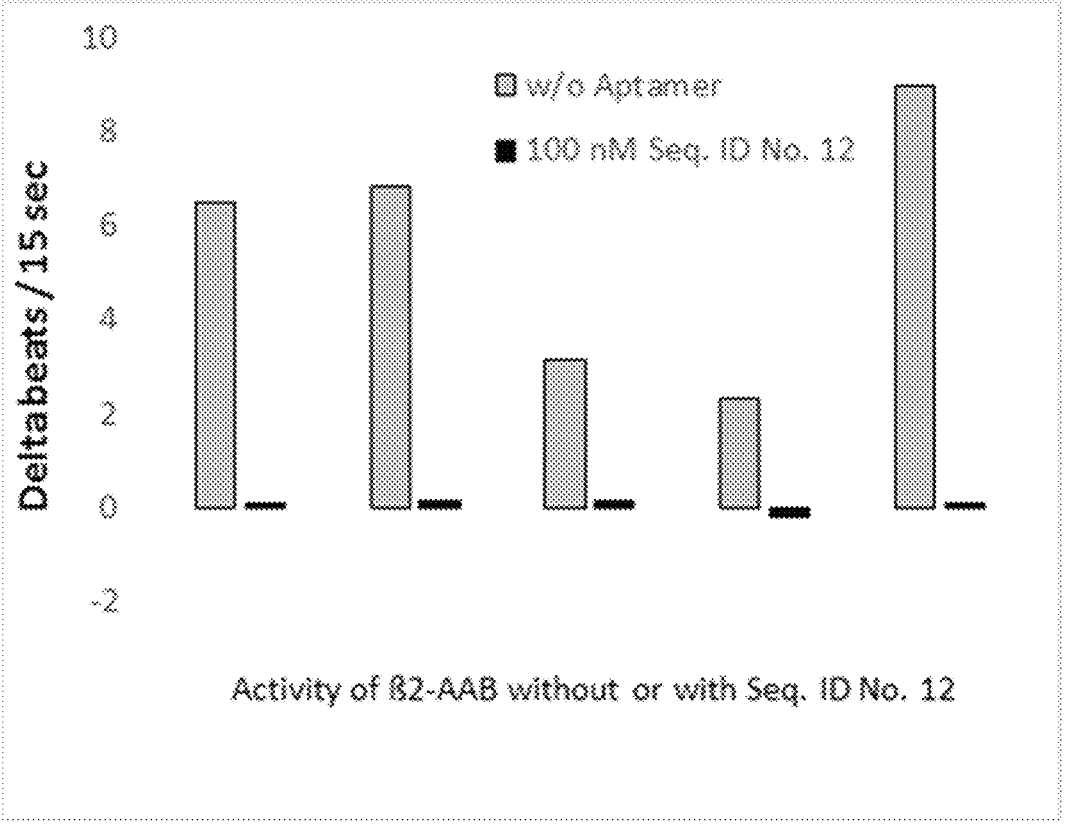
FIG. 14 shows the activity of beta 2 adrenoceptor AABs isolated from patients suffering from glaucoma, schizophrenia, Chagas' cardiomyopathy, hemolytic-uremic syndrome (EHEC) or Alzheimer's disease (from left to right) in the absence or presence of 100 nM of the inventive aptamer of SEQ ID No.: 12.
Figure 15:
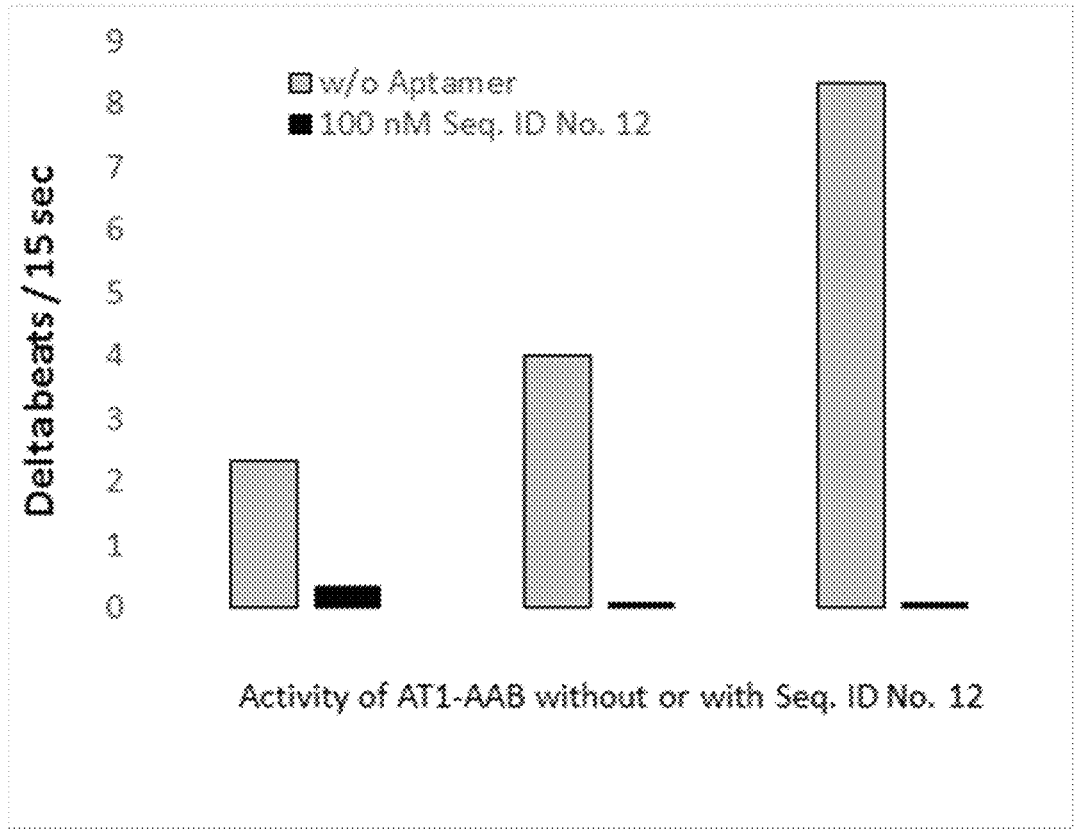
FIG. 15 shows the activity of AT1 AABs isolated from patients suffering from alopecia, kidney allograft rejection or high blood pressure at kidney disease (from left to right) in the absence or presence of 100 nM of the inventive aptamer of SEQ ID No.: 12.
Figure 16:
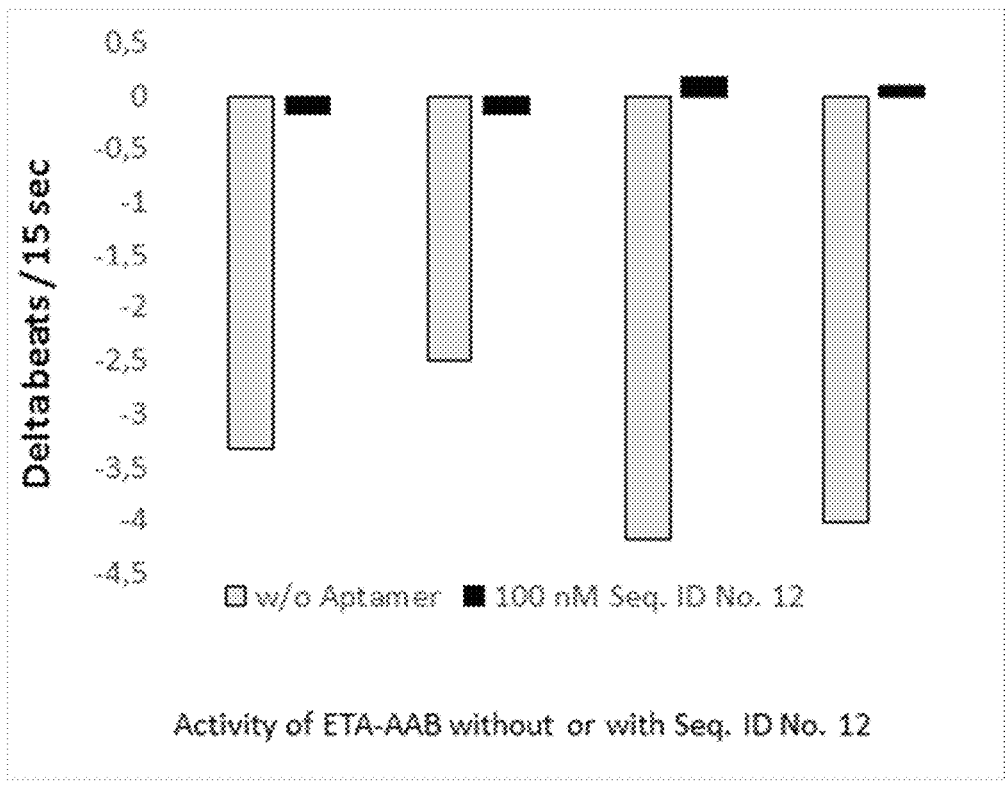
FIG. 16 shows the activity of ETA AABs isolated from patients suffering from pulmonary arterial hypertension, Raynaud's disease, angina pectoris or high blood pressure at kidney disease (from left to right) in the absence or presence of 100 nM of the inventive aptamer of SEQ ID No.: 12.
Figure 17:
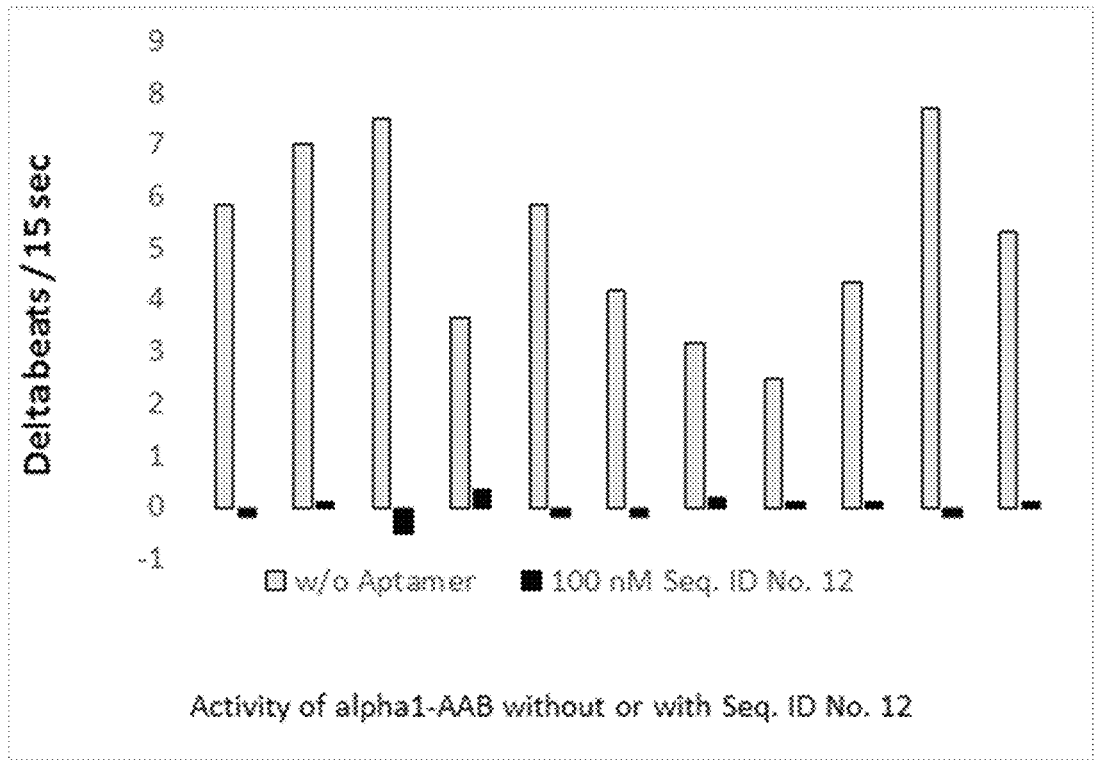
FIG. 17 shows the activity of alpha 1 AABs isolated from patients suffering from pulmonary arterial hypertension, chemotherapy, multiple sclerosis, alopecia, alopecia areata, hemolytic-uremic syndrome (EHEC), Sjöogren's syndrome, Alzheimer's disease, neurodermatitis, Diabetes mellitus Type I or psoriasis (from left to right) in the absence or presence of 100 nM of the inventive aptamer of SEQ ID No.: 12.
Figure 18:
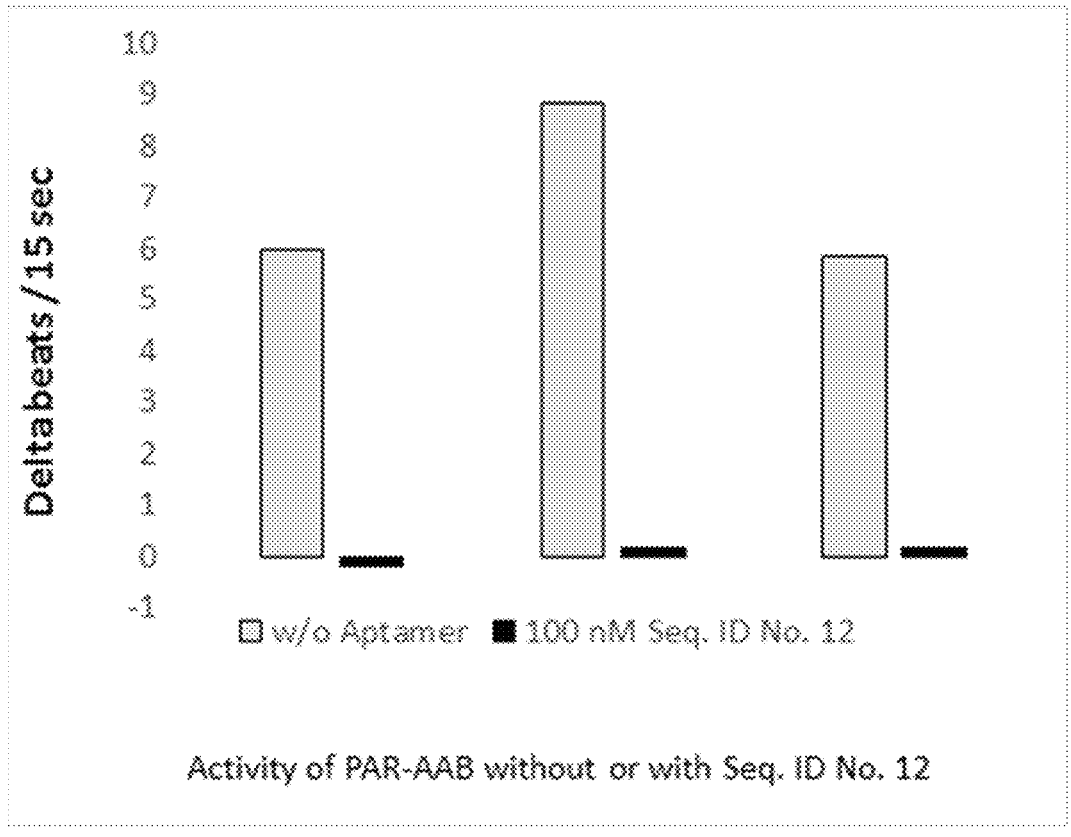
FIG. 18 shows the activity of PAR AABs isolated from patients suffering from Raynaud's disease, angina pectoris or Sjögren's syndrome (from left to right) in the absence or presence of 100 nM of the inventive aptamer of SEQ ID No.: 12.
Figure 19:
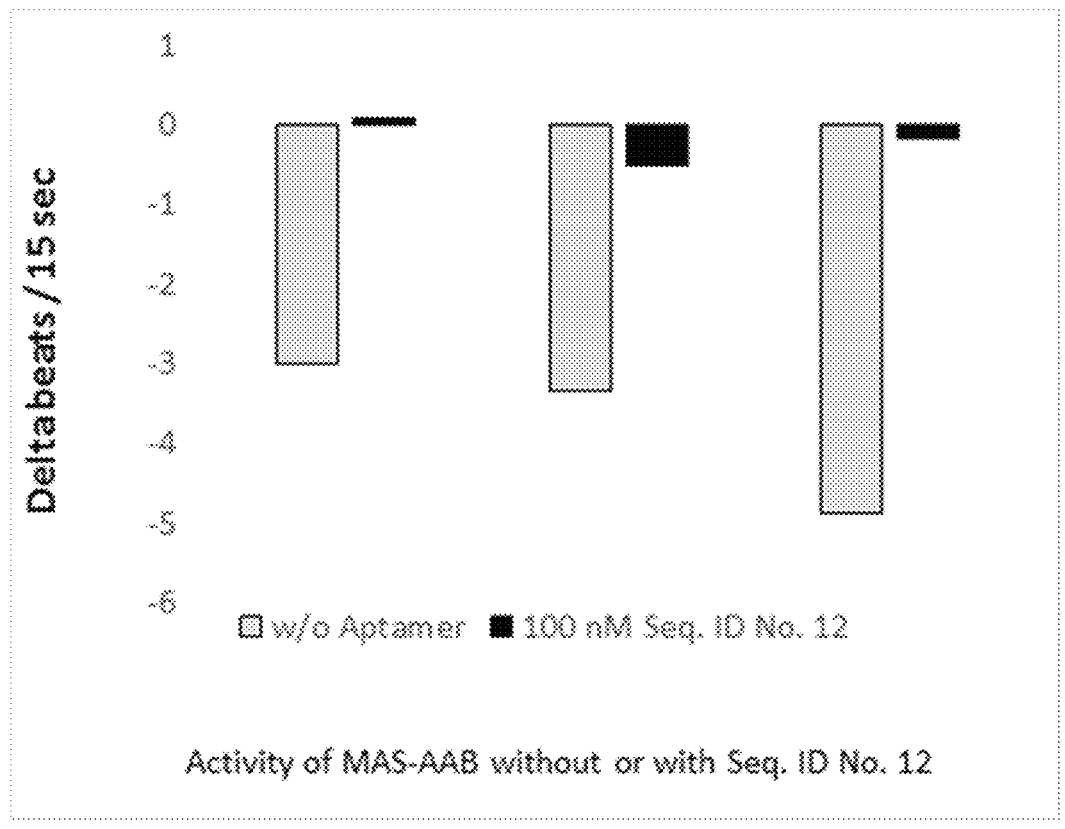
FIG. 19 shows the activity of MAS AABs isolated from patients suffering from chemotherapy, multiple sclerosis or Diabetes mellitus Type I (from left to right) in the absence or presence of 100 nM of the inventive aptamer of SEQ ID No.: 12.

Notably, the inventive aptamer of SEQ ID No: 28 has a sequence identity of 44% to the control sequence SEQ ID No: 48 which is non-functional as will be shown below (see Example 11 and FIG. 12). In contrast, the inventive aptamer of SEQ ID No: 29 shows a very low sequence identity of only 11% to SEQ ID No.: 28, while both sequences are active as will be shown below (see Examples 9 and 10 and FIGS. 10 and 11). This example showing very low sequence identities between inventive sequences and comparatively higher identities to a non-functional sequence (i.e. four times higher) clearly indicates that the activity of the sequences is a function of the commonalities of the sequences represented by the grammar and not of the sequence identity.

These results indicate a clear relationship between sequence properties encoded by the given grammar and the ability of a sequence created or recognized by it to inhibit autoantibodies. This relationship is not based on sequence identities but on the grammar itself which was demonstrated by calculating active sequences with very low mutual sequence identities. In the same way, the comparison of the measured activity of the inventive aptamers with the results of the control sequences confirms the findings regarding the function of all aptamer sequences claimed herein.

The aptamers of the present invention are characterized by satisfying a grammar which is defined by the set of production rules as further defined by claim 1. Said grammar reflects the structural requirements for aptamers which are effective against autoimmune diseases associated with autoantibodies against G-protein coupled receptors.

In a preferred embodiment of the present invention, the aptamer comprises a nucleotide sequence which satisfies a grammar that characterizes a context free language (type 2 grammar in the Chomsky hierarchy) or a context sensitive language (type 1 grammar in the Chomsky hierarchy) or a language (recursively enumerable) which is described by phrase structure grammars (type 0 grammar in the Chomsky hierarchy). In a more preferred embodiment, the aptamer comprises a nucleotide sequence which satisfies a grammar that characterizes a context free language (type 2 grammar in the Chomsky hierarchy).

For the purpose of this invention, the term "aptamer" refers to an oligonucleotide that binds specifically and with high affinity to a target molecule. Under defined conditions, aptamers may fold into a specific three dimensional structure.

The aptamer of the invention comprises or consists of a sequence of nucleic acid molecules, the nucleotides. According to a preferred embodiment, the aptamer of the invention consists of a nucleotide sequence which satisfies the grammar according to the present invention or which consists of a nucleotide sequence otherwise defined herein.

The aptamer of the invention preferably comprises unmodified and/or modified D-and/or L-nucleotides. According to the common one letter code of nucleic acid bases "C" or stands for cytosine, "A" or stands for adenine, "G" or stands for guanine, and "T" or stands for thymine if the nucleotide sequence is a DNA sequence and "T" or stands for a uracil nucleotide if the nucleotide sequence is a RNA sequence. If not indicated below to the contrary, the term "nucleotide" shall refer to ribonucleotides and desoxyribonucleotides.

The aptamer of the invention can comprise or consist of a DNA- or an RNA-nucleotide sequence and, thus, can be referred to as DNA-aptamer or RNA-aptamer, respectively. It is understood that, if the aptamer of the invention comprises an RNA-nucleotide sequence, within the sequence motifs specified throughout the present invention "T" stands for uracil.

For the sake of conciseness throughout the present invention, reference is made solely to explicit DNA-nucleotide sequences. However, it is understood that the respective RNA-nucleotide sequences are also comprised by the present invention.

According to one embodiment, the use of DNA-aptamers is preferred. DNA-aptamers are usually more stable in plasma than RNA-aptamers. However, according to an alternative embodiment, RNA-aptamers are preferred.

The aptamers of the invention may comprise a nucleotide sequence containing 2'-modified nucleotides, e.g. 2'-fluoro-, 2'-methoxy-, 2'-methoxyethyl- and/or 2'-amino-modified nucleotides. The aptamer of the invention may also comprise a mixture of desoxyribonucleotides, modified desoxyribonucleotides, ribonucleotides and/or modified ribonucleotides. Respectively, the terms "2'-fluoro-modified nucleotide", "2'-methoxy-modified nucleotide", "2'-methoxyethyl-modified nucleotide" and/or "2-amino-modified nucleotide" refer to modified ribonucleotides and modified desoxyribonucleotides.

The aptamer of the invention may comprise modifications. Such modifications encompass e.g. alkylation, i.e. methylation, arylation or acetylation of at least one nucleotide, the inclusion of enantiomers and/or the fusion of aptamers with one or more other nucleotides or nucleic acid sequences. Such modifications may comprise e.g. 5'- and/or 3'-PEG- or 5'- and/or 3'-CAP-modifications. Alternatively or in addition, the aptamer of the invention may comprise modified nucleotides, preferably selected from locked-nucleic acids, 2'-fluoro-, 2'-methoxy- and/or 2'-amino-modified nucleotides.

Locked nucleic acids (LNA) represent analogons of the respective RNA nucleotides wherein the conformation has been fixed. Oligonucleotides of locked nucleic acids comprise one or more bicyclic ribonucleosides, wherein the 2'-OH group is connected with the $C_4$-carbon atom via a methylen group. Locked nucleic acids exhibit an improved stability versus nucleases compared to the respective unmodified RNA-aptamer counterparts. Also the hybridization properties are improved which allows for an enhancement of affinity and specificity of the aptamer.

Another preferred modification is the addition of a so called 3'-CAP-, a 5'-CAP-structure and/or of a modified guanosin-nucleotide (e.g. 7-methyl-guanosin) to the 3'- and/or 5'-end of the aptamer. Such a modification of the 3'- and/or 5'-end has the effect that the aptamer is protected from a fast degradation by nucleases.

Alternatively or in addition, the aptamer of the invention can exhibit a pegylated 3' or 5'-end. A 3'- or 5'-PEG modification comprises the addition of at least one polyethylene glycol (PEG) unit, preferably the PEG group comprises 1 to 900 ethylene groups, more preferably from 1 to 450 ethylene groups. In a preferred embodiment, the aptamer comprises linear PEG units with $HO—(CH_2 CH_2O)_n—H$, wherein n is an integer of 1 to 900, preferably n is an integer of 1 to 450.

The aptamer of the invention can comprise or consist of a nucleic acid sequence with a phospho-thioate backbone or can be wholly or in part configured as a peptide nucleic acid (PNA). The aptamers according to the present invention may further be modified as described in Keefe A D et al., Nat Rev Drug Discov. 2010 July; 9(7):537-50 or in Mayer G, Angew Chem Int Ed Engl. 2009; 48(15):2672-89 or in Mayer, G. and Famulok M., Pharmazie in unserer Zeit 2007; 36: 432-436.

Further, the aptamers may be encapsulated in suitable vehicles to protect their structural integrity as well as to promote their delivery inside cells. Preferred vehicles include liposomes, lipid vesicles, microparticles, and the like.

Lipid vesicles resemble plasma membranes, and they can be made to fuse with cell membranes. Most liposomes and multilamellar vesicles are not readily fusogenic, mainly because the stored energy of the vesicle radius of curvature is minimal. Preferred lipid vesicles include small unilamellar vesicles. The small unilamellar vesicles contemplated for encapsulating the aptamers of the present invention are very fusogenic, because they have a very tight radius of curvature. The average diameter of a small unilamellar vesicle is 5 nm to 500 nm; preferably 10 nm to 100 nm, more preferably 20 nm to 60 nm, including 40 nm. This size allows vesicles to pass through the gaps between endothelial cells, thereby permitting systemic delivery of aptamer-containing vesicles following intravenous administration. Useful vesicles may vary greatly in size and are selected according to a specific application with an aptamer.

Small unilamellar vesicles can be readily prepared in vitro using procedures available in the art (as for example disclosed in WO 2005/037323 A2). The compositions from which the vesicles are formed contain a phospholipid which is a stable vesicle former, preferably together with another polar lipid, and optionally with one or more additional polar lipids and/or raft formers. Preferred phospholipids that are stable vesicle formers include 1-palmitoyl-2-docosahexaenoyl-sn-glycero-3-phosphocholine and 1,2-dioleoyl-snglycero-3-phosphocholine. Preferred polar lipids include: 1-palmitoyl-2-oleoyl-sn-glycero-3-phosphate, 1,2-dioleoyl-sn-glycero-3-ethylphosphocholine, 1,2-dioleoyl-sn-glycero-3-phosphoethanolamine, 1,2-dioleoyl-sn-glycero-3-[phospho-l-serine], a typical sphingomyelin, 1,2-dimyristoyl-sn-glycerol, and 1-palmitoyl-2-hydroxy-sn-glycero-3-phosphocholine.

Other preferred polar lipids include phosphatidylserine, phosphatidylglycerol, mixed chain phosphatidylcholine, phosphatidylethanol, and phospholipids containing decosahexaenoic acids. One example of a preferred raft former is cholesterol.

One advantage of modifying the aptamer of the invention by one of the ways mentioned above is that the aptamer can be stabilized against detrimental influences like e.g. nucleases present in the environment wherein the aptamer is used. Said modifications are also suitable to adapt the pharmacological properties of the aptamer. The modifications preferably do not alter the affinity or specificity of the aptamer.

The aptamer of the invention may also be conjugated to a carrier molecule and/or to a reporter molecule. Carrier molecules comprise such molecules that, when conjugated to the aptamer, prolong the plasma half-life of the conjugated aptamer in human plasma, e.g. by enhancing the stability and/or by affecting the excretion rate. One example of a suitable carrier molecule is PEG.

Reporter molecules comprise molecules that allow for the detection of the conjugated aptamer. Examples of such reporter molecules are GFP, biotin, cholesterol, dyes like e.g. fluorescence dyes, electrochemically active reporter molecules and/or compounds comprising radioactive residues, in particular radionuclides suitable for PET (positron emission tomography) detection like e.g. $^{18}F$, $^{11}C$, $^{13}N$, $^{15}O$, $^{82}Rb$ or $^{68}Ga$. The skilled person is well aware of suitable carrier and reporter molecules and of ways of how to conjugate them to the aptamer of the invention.

In a preferred embodiment, the nucleotide sequence of the aptamer of the present invention has a length of at least 4 nucleotides, more preferably at least 8 nucleotides, even more preferably of at least 12 nucleotides and even more preferably at least 16 nucleotides. In another preferred embodiment, the nucleotide sequence of the aptamer of the present invention has a length of at most 120 nucleotides, more preferably of at most 100 nucleotides, even more preferably of at most 80 nucleotides and even more preferably of at most 60 nucleotides. According to one embodiment, the nucleotide sequence of the aptamer of the present invention has a length of at most 40 nucleotides, in particular of at most 20 nucleotides.

According to the present invention, the aptamer does not consist of or comprise any of the nucleotide sequences GGTTGGTGTGGTTGG (SEQ ID No: 22), GGTTGGTGTGGT (SEQ ID NO: 23) or CGCCTAGGTTGGGTAGGGTGGTGGCG (SEQ ID No: 24). This proviso should be applied to any definition of an aptamer or a group of aptamers according to the present invention as described or defined herein.

According to a preferred embodiment, the aptamer of the present invention does not consist of or comprise any of the nucleotide sequences SEQ ID NO: 22, 23 or 24 or any sequence which is more than 90% identical to any of the nucleotide sequences SEQ ID NO: 22, 23 or 24. According to another preferred embodiment, the aptamer of the present invention does not consist of or comprise any of the nucleotide sequences SEQ ID NO: 22, 23 or 24 or any sequence which is more than 85% identical to any of the nucleotide sequences SEQ ID NO: 22, 23 or 24. According to one specific embodiment, the aptamer of the present invention does not consist of or comprise any of the nucleotide sequences SEQ ID NO: 22, 23 or 24 or any sequence which is at least 80% identical to any of the nucleotide sequences SEQ ID NO: 22, 23 or 24.

According to another preferred embodiment of the present invention, aptamer sequences form part of the invention which consist of or comprise a nucleic acid sequence being at least 85% identical to the individualized aptamer sequences which are disclosed herein, more preferably at least 90% identical, even more preferred at least 95% identical.

The determination of percent identity between two sequences is accomplished according to the present invention by using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

According to a preferred embodiment of the present invention, the nucleotide sequence comprised in the aptamer is any one of the following sequences: (5'-GTTGTTTGGGGTGG-3' SEQ ID No: 1), (5'-GTTGTTTGGGGTGGT-3' SEQ ID No: 2), (5'-GGTTGGGGTGGGTGGGGTGGGTGGG-3' SEQ ID No: 3), (5'-TTTGGTGGTGGTGGTTGTGGTGGTGGTG-3' SEQ ID No: 4), (5'-TTTGGTGGTGGTGGTTGTGGTGGTGGTGG-3' SEQ ID No: 5), (5'-TTTGGTGGTGGTGGTTTTGGTGGTGGTGG-3' SEQ ID No: 6), (5'-TTTGGTGGTGGTGGTGGTGGTGGTGGTGG-3' SEQ ID No: 7), (5'-TTTGGTGGTGGTGGTTTGGGTGGTGGTGG-3' SEQ ID No: 8), (5'-TGGTGGTGGTGGT-3' SEQ ID No: 9), (5'-GGTGGTGGTGG-3' SEQ ID No: 10), (5'-GGTGGTTGTGGTGG-3' SEQ ID No: 11), (5'-GGTGGTGGTGGTTGTGGTGGTGGTGG-3' SEQ ID No: 12), (5'-GGTGGTGGTGGTTGTGGTGGTGGTGGTTGTG GTGGTGGTTGTGGTGGTGGTGG-3' SEQ ID No: 13), (5'-GGTGGTTGTGGTGGTTGTGGTGGTTGTGGTGG-3' SEQ ID No:14), (5'-TTTGGTGGTGGTGGTTGTGGTGGTGGTGGTTT-3' SEQ ID No: 15), (5'-GGTGGTGGTGTTGTGGTGGTGGTGGTTT-3' SEQ ID No: 16), (5'-TTTGGTGGTGGTGGTGTGGTGGTGGTGG-3' SEQ ID No: 17), (5'-TGGTGGTGGT-3' SEQ ID No: 18), (5'-TTAGGGTTAGGGTTAGGGTTAGGG (SEQ ID NO: 20). According to another preferred embodiment, the aptamer of the invention has one of the aforementioned nucleotide sequences.

According to a more preferred embodiment, the nucleotide sequence comprised in the aptamer is any one of the following sequences: (5'-GTTGTTTGGGGTGGT-3' SEQ ID No: 2), (5'-GGTTGGGGTGGGTGGGGTGGGTGGG-3' SEQ ID No: 3), (5'-GGTGGTGGTGG-3' SEQ ID No: 10), (5'-GGTGGTGGTGGTTGTGGTGGTGGTGG-3' SEQ ID No: 12), (5'-

TTTGGTGGTGGTGGTTGTGGTGGTGGTGGTTT-3' SEQ ID No: 15). According to another more preferred embodiment, the aptamer of the invention has one of the aforementioned nucleotide sequences.

According to a particularly preferred embodiment, the aptamer comprises the nucleotide sequence (5'-GGTGGTGGTGGTTGTGGTGGTGGTGG-3' SEQ ID No. 12). According to another particularly preferred embodiment, the aptamer has the nucleotide sequence (5'-GGTGGTGGTGGTTGTGGTGGTGGTGG-3' SEQ ID No. 12).

According to a different preferred embodiment of the present invention, the nucleotide sequence comprised in the aptamer is any one of the following sequences: (5'-GCGGTGGTGGGATGGGTTGGATCCGC-3' SEQ ID No: 25), (5'-GGGTCGGGATCTAGGGTCAGG-3' SEQ ID No: 26), (5'- GGTGGGTCGGTAGGGTTT-3' SEQ ID No: 27), (5'- TTGGCTGGATCGGACGGT-3' SEQ ID No: 28), (5'-GGTCGGGTTCGGTGGTTA-3' SEQ ID No: 29), (5'-GG-GATCGGTTCGGTAGGTGGGTGGGTTGG-3' SEQ ID No: 30), (5'-GGCCGGCGCGGCCGG -3' SEQ ID No: 31), (5'-GGAAGGATCGGAAGG-3' SEQ ID No: 32), (5'-GGTAGGCTCGGTAGG-3' SEQ ID No: 33), (5'-GGATGGTTAGGATGG-3' SEQ ID No: 34), (5'-CCGTCGGTCCGTTCGGTATTTTTTTCTGGG TGGCTGAGGATCG-3' SEQ ID No: 35), (5'-GGGTTGGTCCGTTGGGTATTTTTTTATGGG TTGCCTGGTTGGG-3' SEQ ID No: 36), (5'-TCC-CATCGGGTAGGGTTATTTGGGTTCTGGGTGGCT-GAGGATCGATC-3' SEQ ID No: 37), (5'-TGGCGGTGGT-3' SEQ ID No: 38), (5'-TGGAGGTGGA-3' SEQ ID No: 39), (5'-AGGTGGTGGA-3' SEQ ID No: 40), (5'-AGGTGGCGGA-3' SEQ ID No: 41), (5'-GTGGTGGTGGTGTTGGTGGTGGTGGG-3' SEQ ID No: 42), (5'-TGGGTTGGGTTGTTGTTGTTGGGTTGGGT-3' SEQ ID No: 43), (5'-GGTGGTGGTGGTGGTTGGTTTTTGGTTGG TGGTGGTGGTGG-3' SEQ ID No: 44), (5'-CTGGGGTTGGGTTTGGTTTTGTTTTGGTTT GGGTTGGGGTC-3' SEQ ID No: 45). According to another preferred embodiment, the aptamer of the invention has one of the aforementioned nucleotide sequences.

According to a more preferred embodiment, the nucleotide sequence comprised in the aptamer is any one of the following sequences: 5'- GGTGGGTCGGTAGGGTTT-3' SEQ ID No: 27), (5'- TTGGCTGGATCGGACGGT-3' SEQ ID No: 28), (5'-GGTCGGGTTCGGTGGTTA-3' SEQ ID No: 29), (5'-TGGCGGTGGT-3' SEQ ID No: 38), (5'-TG-GAGGTGGA-3' SEQ ID No: 39), (5'-AGGTGGTGGA-3' SEQ ID No: 40), (5'-AGGTGGCGGA-3' SEQ ID No: 41). According to another more preferred embodiment, the aptamer of the invention has one of the aforementioned nucleotide sequences.

According to another more preferred embodiment, the nucleotide sequence comprised in the aptamer is any one of the following sequences: 5'-GGTGGGTCGGTAGGGTTT-3' SEQ ID No: 27), (5'-GGTCGGGTTCGGTGGTTA-3' SEQ ID No: 29), (5'-TGGCGGTGGT-3' SEQ ID No: 38), (5'-TGGAGGTGGA-3' SEQ ID No: 39), (5'-AGGTGGTGGA-3' SEQ ID No: 40), (5'-AGGTGGCGGA-3' SEQ ID No: 41). According to another more preferred embodiment, the aptamer of the invention has one of the aforementioned nucleotide sequences.

According to another more preferred embodiment, the nucleotide sequence comprised in the aptamer is any one of the following sequences: 5'-GGTGGGTCGGTAGGGTTT-3' SEQ ID No: 27), (5'-GGTCGGGTTCGGTGGTTA-3'

SEQ ID No: 29), (5'-TGGCGGTGGT-3' SEQ ID No: 38), (5'-TGGAGGTGGA-3' SEQ ID No: 39). According to another more preferred embodiment, the aptamer of the invention has one of the aforementioned nucleotide sequences.

According to a particularly preferred embodiment, the aptamer comprises the nucleotide sequence (5'-TGGCGGTGGT-3' SEQ ID No: 38). According to another particularly preferred embodiment, the aptamer has the nucleotide sequence (5'-TGGCGGTGGT-3' SEQ ID No: 38).

The aptamers of the present invention are useful for the treatment and/or diagnosis of autoimmune diseases associated with autoantibodies against G-protein coupled receptors. In the context of the present invention, the aptamers are considered to be useful for human subjects as well as for animal subjects. According to one embodiment, the aptamers are for use in human subjects. According to another embodiment, the aptamers are for use in animal subjects. According to one preferred embodiment, the aptamers of the present invention are for use in the treatment of autoimmune diseases as defined herein.

Diseases which are associated with autoantibodies against G-protein coupled receptors are diseases in which such autoantibodies can be detected in a patient affected by such a disease using standard methods as known in the art. According to a preferred embodiment, the diseases are caused by autoantibodies against G-protein coupled receptors. According to one embodiment, the state of a patient in which autoantibodies against G-protein coupled receptors can be detected but no further symptoms are apparent may be considered an autoimmune disease associated with autoantibodies against G-protein coupled receptors.

Thus, the aptamers of the present invention are preferably for use in the treatment of patients having antibodies against a G-protein coupled receptor in a body fluid. According to a preferred embodiment of the present invention, the patients to be treated or diagnosed using the aptamers of the present invention are patients in which antibodies against G-protein coupled receptors can be detected.

Several diseases have already been reported or are known in the literature to be associated with autoantibodies against G-protein coupled receptors. The present inventors have conducted further research in view of such an association and have discovered that more diseases than previously reported are associated with such autoantibodies (data not shown).

Due to the affinity of the claimed aptamers to GPCR autoantibodies, any disease which is associated with the presence of such autoantibodies is plausible to be effectively treated with the aptamers presented and claimed herein. Thus, according to a preferred embodiment of the present invention, the autoimmune diseases is one of cardiomyopathy, dilated cardiomyopathy (DCM), ischemic cardiomyopathy (iCM), peripartum cardiomyopathy (PPCM), idiopathic cardiomyopathy, Chagas' cardiomyopathy, chemotherapy-induced cardiomyopathy, Chagas' megacolon, Chagas' megaesophagus, Chagas' neuropathy, benign prostatic hyperplasia, scleroderma, Raynaud syndrome, peripheral artery occlusive disease (PAOD), pre-eclamsia, kidney allograft rejection, myocarditis, glaucoma, hypertension, pulmonary hypertension, malignant hypertension, metabolic syndrome, Alopecia, Alopecia areata, migraine, Parkinson's disease, epilepsia, cluster headache, multiple sclerosis, depression, regional pain syndrome, instable angina pectoris, systemic lupus erythematosus (SLE), schizophrenia, Sjögren's syndrome, periodontitis, atrial fibrillation, vitiligo, hemolytic uremic syndrome, stiff person syndrome, congenital heart block, Diabetes mellitus Type I, psoriasis, Alzheimer's disease, fatigue, neurodermatitis, renal kidney disease, amyotrophic lateral sclerosis (ALS), Leber's hereditary optic neuropathy (LHON syndrome), allergic asthma, arrhythmia, refractory hypertension, Diabetes mellitus Type II, vascular dementia, non-Chagas megacolon and/or orthostatic hypertension.

While the data presented herein demonstrates the association for a wide range of diseases with the target molecules of the aptamers according to the invention, in principle all of the diseases mentioned herein have been recognized by the inventors to be associated with autoantibodies against G-protein coupled receptors and are thus promising target diseases to be treated with the aptamers according to the present invention.

According to a preferred embodiment of the present invention, the autoimmune disease is one of cardiomyopathy, dilated cardiomyopathy (DCM), ischemic cardiomyopathy (iCM), peripartum cardiomyopathy (PPCM), idiopathic cardiomyopathy, Chagas' cardiomyopathy, chemotherapy-induced cardiomyopathy, Chagas' megacolon, Chagas' megaesophagus, Chagas' neuropathy, benign prostatic hyperplasia, scleroderma, Raynaud syndrome, peripheral artery occlusive disease (PAOD), pre-eclamsia, kidney allograft rejection, myocarditis, glaucoma, hypertension, pulmonary hypertension, malignant hypertension, metabolic syndrome, Alopecia, Alopecia areata, migraine, Parkinson's disease, epilepsia, cluster headache, multiple sclerosis, depression, regional pain syndrome, instable angina pectoris, systemic lupus erythematosus (SLE), schizophrenia, Sjögren's syndrome, periodontitis, atrial fibrillation, vitiligo, hemolytic uremic syndrome, stiff person syndrome, and/or congenital heart block, more preferably the autoimmune disease is dilated cardiomyopathy (DCM).

According to another embodiment of the present invention, the autoimmune disease is a heart disease, a neurological disease, a vessel disease, a connective tissue disease (CTD), a skin disease or a Chagas' disease, in particular the autoimmune disease is a heart disease, a neurological disease or a vessel disease. According to one particular embodiment, the autoimmune disease is a heart disease.

A heart disease within the meaning of the present invention may be cardiomyopathy, dilated cardiomyopathy, ischemic cardiomyopathy, idiopathic cardiomyopathy, peripartum cardiomyopathy, Chagas' cardiomyopathy, atrial fibrillation, acute and chronic myocarditis, congenital heart block, instable angina pectoris, chemotherapy induced cardiomyopathy or hypertrophic cardiomyopathy.

A neurological disease within the meaning of the present invention may be migraine, depression, epilepsia, Parkinson's disease, multiple sclerosis, cluster headache, schizophrenia, stiff man syndrome, Chagas' neuropathy or complex regional pain syndrome.

A vessel disease within the meaning of the present invention may be hypertension, pulmonary hypertension, peripheral artery occlusive disease, malignant hypertension or Raynaud syndrome.

A connective tissue disease (CTD) within the meaning of the present invention may be scleroderma, systemic lupus erythematosus SLE or Sjögren's syndrome. A skin disease within the meaning of the present invention may be alopecia areata, alopecia or vitiligo. A Chagas' disease within the meaning of the present invention may be Chagas' megacolon or Chagas' megaesophagus.

In an alternative embodiment, the autoimmune disease is one of glaucoma, metabolic syndrome, periodontitis, hemolytic uremic syndrome, pre-eclamsia, benign prostatic hyperplasia or kidney allograft rejection.

According to another alternative embodiment, the auto-immune disease is one of dilated cardiomyopathy, idiopathic cardiomyopathy, acute and chronic myocarditis, Chagas' cardiomyopathy, peripartum cardiomyopathy, pulmonary hypertension, hypertension, pre-eclamsia, malignant hyper-tension, instable angina pectoris, ischemic cardiomyopathy, migraine, depression, multiple sclerosis, Parkinson's disease or epilepsy, in particular one of dilated cardiomyopathy, idiopathic cardiomyopathy, acute and chronic myocarditis, Chagas' cardiomyopathy, peripartum cardiomyopathy, pul-monary hypertension or hypertension, optionally one of dilated cardiomyopathy, idiopathic cardiomyopathy or acute and chronic myocarditis.

In particular, the aptamers of the present invention are capable to interact with an autoantibody, preferably an autoantibody which is specific for a G-protein coupled receptor, preferably specific for any one of the human G-protein coupled receptors adrenergic alpha-1 receptor, adrenergic beta-1 receptor, adrenergic beta-2 receptor, endothelin 1 ETA receptor, muscarinic M2 receptor, angio-tensin II AT1 receptor, PAR receptors, MAS-receptor, 5HT4-receptor and/or M3-receptor and more preferably capable of inhibiting the specific interaction of these autoan-tibodies with its target proteins.

Herein, the adrenergic beta1-receptor may also be indi-cated as beta1-receptor, β1-AR or beta1-R. Further, the adrenergic beta2-receptor may also be indicated as beta1-receptor, β2-AR or beta2-R. Also, the angiotensin II recep-tor, Type I may be named angiotensin II AT1 receptor, angiotensin AT1 receptor or AT1-R. The endothelin 1 ETA receptor may be indicated as ETA-R or ETA-1-R and the adrenergic alpha1-receptor may also be indicated as alpha1-receptor, α1-AR or alpha1-R. The protease-activated recep-tors may be named PAR-R. The Angiotensin-II metabolite angiotensin (1-7) binding receptor may be named herein as mas-related G-protein coupled receptor A, MAS receptor, MAS-R or MASI . The 5-hydroxytryptamine receptor 4 may be abbreviated to 5HT4-R while the muscarinic receptors may be indicated as $M_X$-R with the x indicating the subtype of the muscarinic receptor.

According to one embodiment of the present invention, the muscarinic M receptor is meant to encompass the M1, M2, M3 and/or M4 receptor. According to another embodi-ment, the muscarinic M1, M2, M3 and/or M4-receptors are useful as specific examples where the M3 receptor is given as an example for a G-protein coupled receptor against which autoantibodies may be directed.

As shown below exemplarily for the aptamer having the sequence of SEQ ID No: 12, the aptamers of the present invention can be used to neutralize the whole spectrum of autoantibodies specific for G-protein coupled receptors. In Examples 12 to 20 herein, this aptamer is shown to specifi-cally neutralize various autoantibodies taken from patients suffering from autoimmune diseases associated with these autoantibodies (see FIGS. 13 to 21). Thus, it is plausible that the aptamers according to the invention are able to neutralize autoantibodies against G-protein coupled receptors and thus effective in the treatment of diseases wherein such autoan-tibodies are present in a patient suffering from such a disease.

By inhibiting the pathological behavior of the autoanti-bodies directed against the G-protein coupled receptors, the neutralizing effect of the aptamers of the invention dimin-ishes, or even abolishes the permanent activation of the respective G-protein coupled receptors. As a consequence, there is no need for a complicated removal of these anti-bodies. Thus, the present invention provides a collection of compounds that are suitable for use in treatment and/or diagnosis of autoimmune diseases associated with the pres-ence of autoantibodies which recognize G-protein coupled receptors, namely autoimmune diseases associated with the presence of autoantibodies specific for adrenergic alpha-1 receptor, adrenergic beta-1 receptor, adrenergic beta-2 receptor, endothelin 1 ETA receptor, muscarinic M2 recep-tor, angiotensin II AT1 receptor, PAR receptors, MAS-receptor, 5HT4-receptor and/or M3-receptor.

Furthermore after immobilization, the aptamers of the present invention are capable of catching or immobilizing the autoantibiodies indicated above. Thus, a platform is provided to establish an apheresis technology for clearing patient's serum from the autoantibodies and to develop an analytical tool for the measurement of the autoantibodies. The last can be used in particular for diagnosis of autoim-mune diseases.

According to a preferred embodiment, the aptamers of the present invention are for use in the diagnosis of an autoim-mune disease as defined herein. In particular, the aptamers are for use in in vitro detection of an antibody being specific for a G-protein coupled receptor, preferably the human G-protein coupled receptor adrenergic alpha-1 receptor, adrenergic beta-1 receptor, adrenergic beta-2 receptor, endothelin 1 ETA receptor, muscarinic M receptor, angio-tensin II AT1 receptor, PAR receptors, MAS-receptor, 5HT4-receptor and/or M3 receptor. According to another preferred embodiment, the aptamers of the present invention are for use in in vivo diagnosis of an autoimmune disease as defined herein. According to a more preferred embodiment, the antibody to be detected is an autoantibody.

As used herein, "autoantibody" means an antibody formed in response to, and reacting against, an antigenic constituent of a patients own tissues. Such an antibody may attack the cells, tissues, or native proteins of the organism in which it was formed and is usually affiliated with a patho-genic process in said organism.

According to a preferred embodiment, the antibody which is specific for a G-protein coupled receptor is present in or derived from a body fluid, preferably a fluid of a human body, more preferably of human blood, plasma, serum, urine, feces, synovial fluid, interstitial fluid, lymph, saliva, spinal fluid and/or lacrimal fluid. More preferably, the body fluid is taken from an individual suffering from or suspected to suffer from an autoimmune disease, preferably an auto-immune disease associated with presence in the serum of the patient of autoantibodies specific for a G protein coupled receptor, more preferably autoimmune diseases associated with presence in the serum of the patient of autoantibodies specific for adrenergic alpha-1 receptor, adrenergic beta-1 receptor, adrenergic beta-2 receptor, endothelin 1 ETA receptor, muscarinic M receptor, angiotensin II AT1 recep-tor, PAR receptors, MAS-receptor, 5HT4-receptor and/or M3 receptor.

The aptamer of the invention, when used for treatment or diagnosis of an autoimmune disease does not necessarily need to be administered to an individual or patient. The therapeutic or diagnostic effect may also be achieved by use of the aptamer of the invention for elimination of antibodies, like e.g. autoantibodies from the body or from body fluids.

Such an elimination may comprise the application of the aptamer of the invention in a setting where the aptamer of the invention is contacted with a body fluid solely ex vivo, e.g. during immune adsorption and/or apheresis, so that the aptamer of the invention does not enter the body of the individual or patient to be treated. Thus, the present invention is also directed to an apheresis column comprising an aptamer of the present invention.

Apheresis is a medical technology in which the blood of a donor or patient is passed through an apparatus that separates out one particular constituent and returns the remainder back to the circulation of the donor or patient. Thus, apheresis is conducted by linking the patient's plasma, the patient's body and the means achieving the therapeutic effect, i.e. the aptamer bound to the column, in a closed circuit. The aptamer of the invention can be used as selective ingredient during apheresis. The selective ingredient is responsible for specifically separating out the desired particular constituents, namely the antibodies or autoantibodies present in the sample or blood which are specifically targeted by the aptamer of the invention.

Preferably the aptamer of the invention is used for treatment and/or diagnosis of an autoimmune disease, wherein the autoimmune disease is cardiomyopathy, dilated cardiomyopathy (DCM), ischemic cardiomyopathy (iCM), peripartum cardiomyopathy (PPCM), idiopathic cardiomyopathy, Chagas' cardiomyopathy, chemotherapy-induced cardiomyopathy, Chagas' megacolon, Chagas' megaesophagus, Chagas' neuropathy, benign prostatic hyperplasia, scleroderma, Raynaud syndrome, peripheral artery occlusive disease (PAOD), pre-eclamsia, kidney allograft rejection, myocarditis, glaucoma, hypertension, pulmonary hypertension, malignant hypertension, metabolic syndrome, Alopecia, Alopecia areata, migraine, Parkinson's disease, epilepsia, cluster headache, multiple sclerosis, depression, regional pain syndrome, instable angina pectoris, systemic lupus erythematosus (SLE), schizophrenia, Sjögren's syndrome, periodontitis, atrial fibrillation, vitiligo, hemolytic uremic syndrome, stiff person syndrome, and/or congenital heart block. Further preferably, the aptamer of the invention is used as selective ingredient for therapeutic apheresis of blood or parts thereof derived from a patient suffering from an autoimmune disease as further defined herein.

The present invention also relates to an aptamer of the invention coupled to a solid support. The skilled person is well aware of techniques and materials which may be used to produce such aptamers coupled to a solid support. In a preferred embodiment, the solid support comprises a solid material that is applicable in medical, biochemical or biological assays.

Said solid material comprises polymers that are usually used as support in medical, biochemical or biological assays. In particular, the aptamer of the invention may be coupled to a solid support that allows for the use of the resulting product in the manufacturing of a column suitable for apheresis, preferably a column that is suitable for use in an apheresis to remove antibodies specific for a G-protein coupled receptor from a liquid sample, preferably from a body fluid.

The manufacturing or mass production of aptamers of the invention is well known in the art and represents a mere routine activity.

The present invention is also directed to a pharmaceutical composition comprising at least one aptamer of the invention and, optionally, at least one pharmaceutically acceptable excipient. The invention is also directed to a pharmaceutical composition comprising an aptamer of the invention or a mixture of different aptamers of the invention and a pharmaceutically acceptable excipient like e.g. a suitable carrier or diluent.

Preferably, the aptamer of the invention constitutes an active ingredient of the pharmaceutical composition and/or is present in an effective amount. The term "effective amount" denotes an amount of the aptamer of the invention having a prophylactically, diagnostically or therapeutically relevant effect on a disease or pathological condition. A prophylactic effect prevents the outbreak of a disease. A therapeutically relevant effect relieves to some extent one or more symptoms of a disease or returns to normal either partially or completely one or more physiological or biochemical parameters associated with or causative of the disease or pathological conditions.

The respective amount for administering the aptamer of the invention is sufficiently high in order to achieve the desired prophylactic, diagnostic or therapeutic effect. It will be understood by the skilled person that the specific dose level, frequency and period of administration to any particular mammal will depend upon a variety of factors including the activity of the specific components employed, the age, body weight, general health, sex, diet, time of administration, route of administration, drug combination, and the severity of the specific therapy. Using well-known means and methods, the exact amount can be determined by one of skill in the art as a matter of routine experimentation.

According to one embodiment of the pharmaceutical composition of the invention at least 20% of the total aptamer content is made of an aptamer of the invention, preferably at least 50%, more preferably at least 75%, most preferable at least 95%.

When used for therapy, the pharmaceutical composition will generally be administered as a formulation in association with one or more pharmaceutically acceptable excipients. The term "excipient" is used herein to describe any ingredient other than the aptamer of the invention.

The choice of excipient will to a large extent depend on the particular mode of administration. Excipients can be suitable carriers and/or diluents.

The pharmaceutical composition of the invention may be administered orally. Oral administration may involve swallowing, so that the composition enters the gastrointestinal tract, or buccal or sublingual administration may be employed by which the composition enters the blood stream directly from the mouth.

Formulations suitable for oral administration include: solid formulations such as tablets; coated tablets, capsules containing particulates, liquids, or powders; lozenges (including liquid-filled); and chews; multi- and nano-particulates; gels; solid solutions; liposomes; films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

For tablet dosage forms, depending on dose, the aptamer of the invention may make up from 0.1 weight % to 80 weight % of the dosage form, more typically from 5 weight % to 60 weight % of the dosage form. In addition to the aptamer of the invention, tablets generally contain a disintegrant.

Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate.

Generally, the disintegrant will comprise from 1 weight % to 25 weight %, preferably from 5 weight % to 20 weight % of the dosage form.

Tablets may comprise additional excipients like e.g. binders, surface active agents, lubricants and/or other possible ingredients like e.g. anti-oxidants, colorants, flavouring agents, preservatives and/or taste-masking agents.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

Solid formulations for oral administration may be formulated to be immediate and/or modified release. Modified release formulations include delayed-, sustained-, pulsed-, controlled-, targeted and programmed release.

The pharmaceutical composition of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of pharmaceutical composition of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLApoly(dl-lactic-coglycolic)acid (PGLA) microspheres.

The pharmaceutical composition of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions.

Liposomes may also be used. Typical carriers include alcohol, water, mineral oil, liquid petrolatum, white petrolatum, glycerin, polyethylene glycol and propylene glycol. Penetration enhancers may be incorporated. Other means of topical administration include delivery by electroporation, iontophoresis, phonophoresis, sonophoresis and microneedle or needle-free (e.g. Powderject™, Bioject™, etc.) injection. Formulations for topical administration may be formulated to be immediate and/or modified release. Modified release formulations include delayed-, sustained-, pulsed-, controlled-, targeted and programmed release.

For administration to human patients, the total daily dose of the aptamer of the invention and/or the pharmaceutical composition of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 75 kg to 80 kg. The physician will readily be able to determine doses for subjects whose weight falls outside this range, such as infants and the elderly.

The present invention also encompasses a kit comprising an aptamer of the invention, a pharmaceutical composition, a container and optionally written instructions for use and/or with means for administration.

For treatment and/or diagnosis of a disease, irrespective of the route of administration, the aptamer of the invention is administered at a daily dose per treatment cycle of not more than 20 mg/kg body weight, preferably of not more than 10 mg/kg body weight, more preferably selected from the range of 1 µg/kg to 20 mg/kg body weight, most preferably selected from a range of 0.01 to 10mg/kg body weight.

In one embodiment, the present invention is directed to the aptamer of the invention for use in the in vitro detection and/or characterization of antibodies, like e.g. autoantibodies, being specific for a G-protein coupled receptor, preferably the G-protein coupled receptors adrenergic alpha-1 receptor, adrenergic beta-1 receptor, adrenergic beta-2 receptor, endothelin 1 ETA receptor, muscarinic M2 receptor, angiotensin II AT1 receptor, PAR receptors, MAS-receptor, 5HT4-receptor and/or M3-receptor. Accordingly, one preferred embodiment of the present invention is directed to the use of an aptamer as defined in any one of embodiments 1-8 for the in vitro detection of an antibody being specific for a G-protein coupled receptor, preferably the human G-protein coupled receptor adrenergic alpha-1 receptor, adrenergic beta-1 receptor, adrenergic beta-2 receptor, endothelin 1 ETA receptor, muscarinic M receptor, angiotensin II AT1 receptor, PAR receptors, MAS-receptor, 5HT4-receptor and/or M3 receptor.

Such a use may comprise the testing of a sample in a rat cardiomyocyte beating frequency assay in the presence and absence of an effective amount of an aptamer of the invention. Depending on the effect of the sample and the aptamer of the invention on the beating frequency, the skilled person can conclude on the presence of respective antibodies. Data on total or relative quantity of such antibodies in the sample may also be gained as well as on other properties of such antibodies.

The so called rat cardiomyocyte beating frequency assay is a well-established assay for detection and characterization of antibodies, e.g. autoantibodies derived from patients, specific for a number of human G-protein coupled receptors like e.g. human adrenergic alpha-1 receptor, adrenergic beta-1 receptor, adrenergic beta-2 receptor, endothelin 1 ETA receptor, muscarinic M2 receptor, angiotensin II AT1 receptor, PAR receptors, MAS-receptor, 5HT4-receptor and/or M3-receptor.

The assay is described in detail in Wallukat et al. (1987) Effects of the serum gamma globulin fraction of patients with allergic asthma and dilated cardiomyopathy on chromotropic beta adrenoceptor function in cultured neonatal rat heart myocytes, *Biomed. Biochim. Acta* 46, 634 - 639; Wallukat et al. (1988) Cultivated cardiac muscle cells—a functional test system for the detection of autoantibodies against the beta adrenergic receptor, *Acta Histochem.* Suppl. 35, 145- 149; and Wallukat et al. (2010) Distinct patterns of autoantibodies against G-protein coupled receptors in Chagas' cardiomyopathy and megacolon. Their potential impact for early risk assessment in asymptomatic Chagas' patients, *J. Am. Col. Cardiol.* 55, 463 - 468. Thus, the skilled person is well aware of the nature of this assay and knows how to apply it.

For detection and/or characterization of such antibodies, the aptamer of the invention may be used in solution or in an immobilized form.

The aptamer of the invention may be used for direct or indirect detection and/or characterization of said antibodies.

According to another aspect of the present invention, a method for the preparation of an aptamer oligonucleotide is provided comprising the steps of determination of a nucleotide sequence for use as an aptamer sequence comprising the application of the following set of production rules P:

$P = \{$

| | | | |
|---|---|---|---|
| $S$ | $\rightarrow$ | $M \mid Y \mid D \mid E \mid H$ | (1) |
| $M$ | $\rightarrow$ | $NRM$ | (2) |
| $M$ | $\rightarrow$ | $MR$ | (3) |
| $M$ | $\rightarrow$ | $RM$ | (4) |
| $N$ | $\rightarrow$ | $M$ | (5) |
| $D$ | $\rightarrow$ | $YM$ | (6) |
| $E$ | $\rightarrow$ | $VM$ | (6a) |
| $Y$ | $\rightarrow$ | $K \mid KL \mid LK \mid LKL$ | (7) |
| $H$ | $\rightarrow$ | $LV \mid V$ | (8) |
| $R$ | $\rightarrow$ | $L$ | (9) |
| $Z$ | $\rightarrow$ | $A \mid C \mid G \mid T$ | (10) |
| $L$ | $\rightarrow$ | $ZL \mid Z$ | (11) |
| $BX$ | $\rightarrow$ | $G^x$ | (12) |
| $CX$ | $\rightarrow$ | $BXLBX$ | (13) |
| $M$ | $\rightarrow$ | $CXLCX$ | (14) |
| $K$ | $\rightarrow$ | $CXLBX$ | (15) |
| $V$ | $\rightarrow$ | $CXL$ | (16) |

$\}$ with the conditions
a.) Q is the set of natural numbers
b.) F is a subset of natural numbers defined as $F:=\{X \in Q \mid (X>1)\}$ c.) Using F we define:

| | |
|---|---|
| $\forall\, X \in F \exists\, M{:}M \rightarrow CXLCX$ | (1) |
| $\forall\, X \in F \exists\, K{:}K \rightarrow CXLBX$ | (2) |
| $\forall\, X \in F \exists\, V{:}V \rightarrow CXL$ | (3) |

-continued $$\forall\, X \in F{:}CX \rightarrow BXLBX \tag{4}$$

$$\forall\, X \in F{:}BX \rightarrow \prod_{1}^{X} G \tag{5}$$

d.) U is a set of non-terminals defined as

U={S, M, N, D, E, Y, H, R, Z, L, BX, CX, K, V}

For BX and CX see c)
e.) W is a set of non-terminals defined as

W={A, C, G, T, GX}

$G^X$ denotes all terminals which can be derived according to b.) and c.) (5)
f.) S ∈ U is the starting symbol
wherein "A" means an adenine nucleotide, "C" means a cytosine nucleotide, "G" means a guanine nucleotide and "T" means a thymine nucleotide if the nucleotide sequence is a DNA sequence, and "T" means a uracil nucleotide if the nucleotide sequence is a RNA sequence, and producing an aptamer oligonucleotide having the nucleotide sequence obtained in the first step.

According to a preferred embodiment, the step of determination of a nucleotide sequence for use as an aptamer sequence comprises the application of the following consensus sequence $$S_i\text{-}(GGG\text{-}S\text{-}GGG\text{-}S)_n\text{-}(GGG\text{-}S\text{-}GGG)_k\text{-}S_m \tag{1}$$

wherein n>1;
i, m, k=0, 1;
S={A,C,G,T}$^+$ or {A,C,G}$^+$ or {A,C,T}$^+$ or {A,G,T}$^+$ or {C,G,T}$^+$ or {A,C}$^+$ or {A,G}$^+$ or {A,T}$^+$ or {C,G}$^+$ or {C,T}$^+$ or {G,T}$^+$ or {A}$^+$ or {C}$^+$ or {T}$^+$, wherein {}$^+$ denotes the positive Kleene Closure of the given alphabet set.

The term Positive Kleene Closure describes a way of concatenation of members of a finite, nonempty set of symbols (a vocabulary or alphabet). As a result of this process new words (sequences of symbols) will be created. Each word has a length greater than zero.

According to another preferred embodiment of the present invention, an aptamer is provided comprising a nucleotide sequence which satisfies the consensus sequence of formula (1) for use in the treatment and/or diagnosis of autoimmune diseases associated with autoantibodies against G-protein coupled receptors, wherein "A" means an adenine nucleotide, "C" means a cytosine nucleotide, "G" means a guanine nucleotide and "T" means a thymine nucleotide if the nucleotide sequence is a DNA sequence, and "T" means a uracil nucleotide if the nucleotide sequence is a RNA sequence, wherein the aptamer does not comprise the nucleotide sequence CGCCTAGGTTGGGTAGGGTGGTGGCG (SEQ ID No: 24).

According to yet another preferred embodiment, the step of determination of a nucleotide sequence for use as an aptamer sequence comprises the application of the following consensus sequence $$S_i(GG\text{-}S\text{-}GG\text{-}S)_n\text{-}(GG\text{-}S\text{-}GG)_k\text{-}S_m \tag{2}$$

wherein n>1;
i, m, k=0, 1;
S={A,C,G,T}$^+$ or {A,C,G}$^+$ or {A,C,T}$^+$ or {A,G,T}$^+$ or {C,G,T}$^+$ or {A,C}$^+$ or {A,G}$^+$ or {A,T}$^+$ or {C,G}$^+$ or {C,T}$^+$ or {G,T}$^+$ or {A}$^+$ or {C}$^+$ or {T}$^+$, wherein {}$^+$ denotes the positive Kleene Closure of the given alphabet set.

According to another preferred embodiment of the present invention, an aptamer is provided comprising a nucleotide sequence which satisfies the consensus sequence of formula (2) for use in the treatment and/or diagnosis of autoimmune diseases associated with autoantibodies against G-protein coupled receptors, wherein "A" means an adenine nucleotide, "C" means a cytosine nucleotide, "G" means a guanine nucleotide and "T" means a thymine nucleotide if the nucleotide sequence is a DNA sequence, and "T" means a uracil nucleotide if the nucleotide sequence is a RNA sequence, wherein the aptamer does not comprise the nucleotide sequence GGTTGGTGTGGTTGG (SEQ ID No: 22), GGTTGGTGTGGT (SEQ ID NO: 23) or CGCCTAGGTTGGGTAGGGTGGTGGCG (SEQ ID No: 24).

According to another preferred embodiment, the step of determination of a nucleotide sequence for use as an aptamer sequence comprises the application of the following consensus sequence $$S_i\text{-}P\text{-}(LM)_j\text{-}E_k; \tag{3}$$

wherein i, k=0, 1;
  j>=0;
  $P=(G_m\text{-}(X)\text{-}G_m\text{-}(Y)\text{-}G_m\text{-}(Z)\text{-}G_m)$;
  $M=(G_m\text{-}(X)\text{-}G_m(Y)\text{-}G_m\text{-}(Z)\text{-}G_m)$;
  m>1;
  S,L,E,X,Y,Z={A,C,G,T}$^+$ or {A,C,G}$^+$ or {A,C,T}$^+$ or {A,G,T}$^+$ or {C,G,T}$^+$ or {A,C}$^+$ or {A,G}$^+$ or {A,T}$^+$ or {C,G}$^+$ or {C,T}$^+$ or {G,T}$^+$ or {A}$^+$ or {C}$^+$ or {T}$^+$ where {}$^+$ denotes the positive Kleene Closure of the given alphabet set.

According to another preferred embodiment of the present invention, an aptamer is provided comprising a nucleotide sequence which satisfies the consensus sequence of formula (3) for use in the treatment and/or diagnosis of autoimmune diseases associated with autoantibodies against G-protein coupled receptors, wherein "A" means an adenine nucleotide, "C" means a cytosine nucleotide, "G" means a guanine nucleotide and "T" means a thymine nucleotide if the nucleotide sequence is a DNA sequence, and "T" means a uracil nucleotide if the nucleotide sequence is a RNA sequence, wherein the aptamer does not comprise the nucleotide sequence GGTTGGTGTGGTTGG (SEQ ID No: 22), GGTTGGTGTGGT (SEQ ID NO: 23) or CGCCTAGGTTGGGTAGGGTGGTGGCG (SEQ ID No: 24).

According to another preferred embodiment, the step of determination of a nucleotide sequence for use as an aptamer sequence comprises the application of the following consensus sequence $$S_i\text{-}P\text{-}E_j; \tag{4}$$

wherein i, j=0, 1;
  $P=(G_m\text{-}(X)\text{-}G_m\text{-}(Y)\text{-}G_m)$;
  m>1;
  X,Y,S,E={A,C,G,T}$^+$ or {A,C,G}$^+$ or {A,C,T}$^+$ or {A,G,T}$^+$ or {C,G,T}$^+$ or {A,C}$^+$ or {A,G}$^+$ or {A,T}$^+$ or {C,G}$^+$ or {C,T}$^+$ or {G,T}$^+$ or {A}$^+$ or {C}$^+$ or {T}$^+$ where {}$^+$ denotes the positive Kleene Closure of the given alphabet set.

According to another preferred embodiment of the present invention, an aptamer is provided comprising a nucleotide sequence which satisfies the consensus sequence of formula (4) for use in the treatment and/or diagnosis of autoimmune diseases associated with autoantibodies against G-protein coupled receptors, wherein "A" means an adenine nucleotide, "C" means a cytosine nucleotide, "G" means a guanine nucleotide and "T" means a thymine nucleotide if the nucleotide sequence is a DNA sequence, and "T" means a uracil nucleotide if the nucleotide sequence is a RNA sequence, wherein the aptamer does not comprise the nucleotide sequence GGTTGGTGTGGTTGG (SEQ ID No: 22), GGTTGGTGTGGT (SEQ ID NO: 23) or CGCCTAGGTTGGGTAGGGTGGTGGCG (SEQ ID No: 24).

Using the method of the present invention, it is possible to determine nucleotide sequences having the structural patterns which are necessary and sufficient to be effective as therapeutic and/or diagnostic aptamers for use in the treatment and/or diagnosis of autoimmune diseases associated with autoantibodies against G-protein coupled receptors.

Sequences of aptamers of the present invention may be generated by the use of the method according to the present invention. In the following, the derivation of the sequence of SEQ ID No.: 55 according to the present invention is exemplarily shown:

```
Derivation of Sequence #55:
(5'-GGTGGTGGTGGTTGTGGTGGTGGTGG-3')

X = 2

S → M

→ NRM

→ MRM

→ C2LC2RM

→ C2LC2RC2LC2

→ B2LB2LC2RC2LC2

→ B2LB2LB2LB2RC2LC2

→ B2LB2LB2LB2RB2LB2LC2

→ B2LB2LB2LB2RB2LB2LB2

→ GGLB2LB2LB2RB2LB2LB2

→ GGLGGLB2LB2RB2LB2LB2

→ GGLGGLGGLB2RB2LB2LB2

→ GGLGGLGGLGGRB2LB2LB2

→ GGLGGLGGLGGRGGLB2LB2

→ GGLGGLGGLGGRGGLGGLB2

→ GGLGGLGGLGGRGGLGGLGG

→ GGLGGLGGLGGRGGLGGLGG

→ GGZGGLGGLGGRGGLGGLGG

→ GGTGGLGGLGGRGGLGGLGG

→ GGTGGZGGLGGRGGLGGLGG

→ GGTGGTGGLGGRGGLGGLGG

→ GGTGGTGGZGGRGGLGGLGG

→ GGTGGTGGTGGRGGLGGLGG (SEQ ID NO: 10)

→ GGTGGTGGTGGLGGLGGLGG (SEQ ID NO: 10)
```

-continued
→ GGTGGTGGTGGTGGZLGGLGGLGGLGGLGG (SEQ ID NO: 10)

→ GGTGGTGGTGGTGGZZGGLGGLGGLGG (SEQ ID NO: 10)

→ GGTGGTGGTGGTZGGLGGLGGLGG (SEQ ID NO: 51)

→ GGTGGTGGTGGTTGGLGGLGGLGG (SEQ ID NO: 52)

→ GGTGGTGGTGGTTGGZGGLGGLGG (SEQ ID NO: 52)

→ GGTGGTGGTGGTTGGTGGLGGLGG (SEQ ID NO: 53)

→ GGTGGTGGTGGTTGGTGGZGGLGG (SEQ ID NO: 53)

-continued
→ GGTGGTGGTGGTTGGTGGTGGLGG (SEQ ID NO: 54)

→ GGTGGTGGTGGTTGGTGGTGGZGG (SEQ ID NO: 54)

→ GGTGGTGGTGGTTGGTGGTGGTGG SEQ ID NO: 55

Using a Shift-Reduce Parser the sequence of SEQ ID No.: 55 can also be recognized in a pool of randomized sequences as a valid sequence after applying the rules of the grammar listed in the following table. Since the input sequence can be reduced to the start symbol S the sequence is a valid sentence for the defined grammar.

| Sequence | SEQ ID NO: | Action | Stack | Rule |
|---|---|---|---|---|
| GGTGGTGGTGGTTGGTGGTGGTGG | 55 | start | $ | |
| GGTGGTGGTGGTTGGTGGTGGTGG | 55 | shift | GG | |
| GGTGGTGGTGGTTGGTGGTGGT | 56 | reduce | B2 | 12a |
| GGTGGTGGTGGTTGGTGGTGGT | 56 | shift | TB2 | |
| GGTGGTGGTGGTTGGTGGTGG | 54 | reduce | ZB2 | 10 |
| GGTGGTGGTGGTTGGTGGTGG | 54 | reduce | LB2 | 11 |
| GGTGGTGGTGGTTGGTGGTGG | 54 | shift | GGLB2 | |
| GGTGGTGGTGGTTGGTGGT | 57 | reduce | B2LB2 | 12a |
| GGTGGTGGTGGTTGGTGGT | 57 | reduce | C2 | 13a |
| GGTGGTGGTGGTTGGTGGT | 57 | shift | TC2 | |
| GGTGGTGGTGGTTGGTGG | 53 | reduce | ZC2 | 10 |
| GGTGGTGGTGGTTGGTGG | 53 | reduce | LC2 | 11 |
| GGTGGTGGTGGTTGGTGG | 53 | shift | GGLC2 | |
| GGTGGTGGTGGTTGGT | 58 | reduce | B2LC2 | 12a |
| GGTGGTGGTGGTTGGT | 58 | shift | TB2LC2 | |
| GGTGGTGGTGGTTGG | 52 | reduce | ZB2LC2 | 10 |
| GGTGGTGGTGGTTGG | 52 | reduce | LB2LC2 | 11 |
| GGTGGTGGTGGTTGG | 52 | shift | GGLB2LC2 | |
| GGTGGTGGTGGTT | 59 | reduce | B2LB2LC2 | 12a |
| GGTGGTGGTGGTT | 59 | reduce | C2LC2 | 13a |
| GGTGGTGGTGGTT | 59 | reduce | M | 14a |
| GGTGGTGGTGGTT | 59 | shift | TM | |
| GGTGGTGGTGGT | 51 | reduce | ZM | 10 |
| GGTGGTGGTGGT | 51 | reduce | LM | 11 |
| GGTGGTGGTGGT | 51 | shift | TLM | |
| GGTGGTGGTGG | 10 | reduce | ZLM | 11 |
| GGTGGTGGTGG | 10 | reduce | LM | 11 |
| GGTGGTGGTGG | 10 | Reduce | RM | 9 |
| GGTGGTGGTGG | 10 | shift | GGRM | |
| GGTGGTGGT | | reduce | B2RM | 12a |
| GGTGGTGGT | | shift | TB2RM | |

-continued

| Sequence | SEQ ID NO: | Action | Stack | Rule |
|----------|------------|--------|-------|------|
| GGTGGTGG | | reduce | ZB2RM | 11 |
| GGTGGTGG | | reduce | LB2RM | 11 |
| GGTGGTGG | | shift | GGLB2RM | |
| GGTGGT | | reduce | B2LB2RM | 12a |
| GGTGGT | | reduce | C2RM | 13a |
| GGTGGT | | shift | TC2RM | |
| GGTGG | | reduce | ZC2RM | 11 |
| GGTGG | | reduce | LC2RM | 11 |
| GGTGG | | shift | GGLC2RM | |
| GGT | | reduce | B2LC2RM | 12a |
| GGT | | shift | TB2LC2RM | |
| GG | | reduce | ZB2LC2RM | 11 |
| GG | | reduce | LB2LC2RM | 11 |
| GG | | shift | GGLB2LC2RM | |
| $ | | reduce | B2LB2LC2RM | 12 |
| $ | | reduce | C2LC2RM | 13a |
| $ | | reduce | MRM | 14a |
| $ | | reduce | NRM | 5 |
| $ | | reduce | M | 2 |
| $ | | reduce | S | 1 |
| $ | | accepted | | |

Further exemplification of derivation of the claimed aptamer sequences of SEQ ID No.: 3, 10 and 15 according to the present invention is shown below:

```
Derivation of Sequence #3:
(5'-GGTTGGGGTGGGTGGGGTGGGTGGG-3')
X = 3
S → M
  → RM
  → LM
  → LC3LC3
  → ZLC3LC3
  → ZZLC3LC3
  → ZZZLC3LC3
  → ZZZZLC3LC3
  → ZZZZZLC3LC3
  → ZZZZZZLC3LC3
  → ZZZZZZZLC3LC3
  → ZZZZZZZZLC3LC3
  → ZZZZZZZZZC3LC3
  → GZZZZZZZZC3LC3
  → GGZZZZZZZC3LC3
  → GGTZZZZZZC3LC3
  → GGTTZZZZZC3LC3
  → GGTTGZZTTC3LC3
  → GGTTGGZZZC3LC3
  → GGTTGGGZZC3LC3
  → GGTTGGGGZC3LC3
  → GGTTGGGGTB3LB3LC3
```

```
-continued
  → GGTTGGGGTB3LB3LB3LB3
  → GGTTGGGGTGGGLB3LB3LB3        (SEQ ID NO: 60)
  → GGTTGGGGTGGGZB3LB3LB3        (SEQ ID NO: 60)
  → GGTTGGGGTGGGTB3LB3LB3        (SEQ ID NO: 61)
  → GGTTGGGGTGGGTGGGLB3LB3       (SEQ ID NO: 62)
  → GGTTGGGGTGGGTGGGZLB3LB3      (SEQ ID NO: 62)
  → GGTTGGGGTGGGTGGGZZB3LB3      (SEQ ID NO: 62)
  → GGTTGGGGTGGGTGGGGZB3LB3      (SEQ ID NO: 63)
  → GGTTGGGGTGGGTGGGGTB3LB3      (SEQ ID NO: 64)
  → GGTTGGGGTGGGTGGGGTGGGLB3     (SEQ ID NO: 65)
  → GGTTGGGGTGGGTGGGGTGGGZB3     (SEQ ID NO: 65)
  → GGTTGGGGTGGGTGGGGTGGGTB3     (SEQ ID NO: 66)
  → GGTTGGGGTGGGTGGGGTGGGTGGG    SEQ ID NO: 3
```

```
Derivation of Sequence #10:
(5'-GGTGGTGGTGG-3')
X = 2
S → M
  → C2LC2
  → B2LB2LC2
  → GGLB2LC2
  → GGZB2LC2
  → GGTB2LC2
  → GGTGGLC2
  → GGTGGZC2
  → GGTGGTC2
  → GGTGGTB2LB2
  → GGTGGTGGLB2
```

```
                    -continued
    → GGTGGTGGZB2
    → GGTGGTGGTB2
    → GGTGGTGGTGG  SEQ ID NO: 10

Derivation of Sequence #15:
(5'-TTTGGTGGTGGTGGTTGTGGTGGTGGTGGTTT-3')
X = 2
S → M
    → RM
    → RNRM
    → RNRMR
    → RMRMR
    → LMRMR
    → ZLMRMR
    → ZZLMRMR
    → ZZZMRMR
    → TZZMRMR
    → TTZMRMR
    → TTTMRMR
    → TTTC2LC2RMR
    → TTTB2LB2LC2RMR
    → TTTGGLB2LC2RMR
    → TTTGGLB2LC2RMR
    → TTTGGZB2LC2RMR
    → TTTGGTB2LC2RMR
    → TTTGGTGGLC2RMR
    → TTTGGTGGZC2RMR
    → TTTGGTGGTC2RMR
    → TTTGGTGGTB2LB2RMR
    → TTTGGTGGTGGLB2RMR   (SEQ ID NO: 67)
    → TTTGGTGGTGGZB2RMR   (SEQ ID NO: 67)
    → TTTGGTGGTGGTB2RMR   (SEQ ID NO: 68)
    → TTTGGTGGTGGTGGRMR   (SEQ ID NO: 69)
    → TTTGGTGGTGGTGGLMR   (SEQ ID NO: 69)
    → TTTGGTGGTGGTGGZLMR  (SEQ ID NO: 69)
    → TTTGGTGGTGGTGGZZLMR (SEQ ID NO: 69)
    → TTTGGTGGTGGTGGZZZLMR (SEQ ID NO: 69)
    → TTTGGTGGTGGTGGZZZZMR (SEQ ID NO: 69)
    → TTTGGTGGTGGTGGTZZZMR (SEQ ID NO: 70)
    → TTTGGTGGTGGTGGTTZZMR (SEQ ID NO: 71)
    → TTTGGTGGTGGTGGTTGZMR (SEQ ID NO: 72)
    → TTTGGTGGTGGTGGTTGTMR (SEQ ID NO: 73)
    → TTTGGTGGTGGTGGTTGTC2LC2R (SEQ ID NO: 73)
    → TTTGGTGGTGGTGGTTGTB2LB2LC2R (SEQ ID NO: 73)
    → TTTGGTGGTGGTGGTTGTGGLB2LC2R (SEQ ID NO: 74)
    → TTTGGTGGTGGTGGTTGTGGZB2LC2R (SEQ ID NO: 74)
    → TTTGGTGGTGGTGGTTGTGGTB2LC2R (SEQ ID NO: 75)
    → TTTGGTGGTGGTGGTTGTGGTGGLC2R (SEQ ID NO: 76)
    → TTTGGTGGTGGTGGTTGTGGTGGZC2R (SEQ ID NO: 76)
    → TTTGGTGGTGGTGGTTGTGGTGGTC2R (SEQ ID NO: 77)
    → TTTGGTGGTGGTGGTTGTGGTGGTB2LB2R (SEQ ID NO: 77)
    → TTTGGTGGTGGTGGTTGTGGTGGTGGLB2R (SEQ ID NO: 78)
    → TTTGGTGGTGGTGGTTGTGGTGGTGGZB2R (SEQ ID NO: 78)
    → TTTGGTGGTGGTGGTTGTGGTGGTGGTB2R (SEQ ID NO: 79)
    → TTTGGTGGTGGTGGTTGTGGTGGTGGTGGR (SEQ ID NO: 5)
    → TTTGGTGGTGGTGGTTGTGGTGGTGGTGGL (SEQ ID NO: 5)
    → TTTGGTGGTGGTGGTTGTGGTGGTGGTGGZL (SEQ ID NO: 5)
    → TTTGGTGGTGGTGGTTGTGGTGGTGGTGGZZL
(SEQ ID NO: 5)
    → TTTGGTGGTGGTGGTTGTGGTGGTGGTGGZZZ
(SEQ ID NO: 5)
    → TTTGGTGGTGGTGGTTGTGGTGGTGGTGGTZZ
(SEQ ID NO: 80)
    → TTTGGTGGTGGTGGTTGTGGTGGTGGTGGTTZ
(SEQ ID NO: 81)
    → TTTGGTGGTGGTGGTTGTGGTGGTGGTGGTTT  SEQ ID NO: 15
```

All embodiments of the present invention as described herein are deemed to be combinable in any combination, unless the skilled person considers such a combination to not make any technical sense.

EXAMPLES

Functional Assay for the Estimation of Autoantibody Activity (Autoantibodies Against G-Protein Coupled Receptors, AAB)

A functional assay able to identify and quantify autoantibodies against G-protein coupled receptors (AAB) was exploited for the estimation of the AAB neutralization capacity of the aptamers of the present invention.

This functional assay exploited spontaneously beating rat cardiomyocytes which were able to respond to patients AABs, when added with aliquots of purified IgG fraction, with a change in their beating frequency—the chronotropic response. The chronotropic response is the sum of positive chronotropy or negative chronotropy caused by stimulating AABs such as the ones targeting adrenergic beta1- , beta2- or -alpha1 receptors, muscarinic M2-receptors and the endothelin receptor type A (ETA-receptor) and is expressed as the difference to the basal beating frequency, delta beat / time.

Inhibiting AABs such as the beta2-adrenoceptor AAB found in patients with allergic asthma, antagonize the positive chronotropic effect induced by beta2-adrenergic agonists.

To differentiate the AAB species with respect to their contribution to the chronotropic response (positive or negative chronotropy), the analysis was conducted in the presence of specific antagonists such as ICI-118.551 for beta2-AAB, atropine for M2-AAB, propranolol for beta1/beta2-AAB, BQ 610 or BQ 123 for the ETA-receptor, prazosine or urapidil for the alpha1-adrenoceptor and Ibesartan or Losartan for the AT1-receptor. The remaining activity change is caused by AAB except the ones which were specifically blocked.

Moreover the specificity of the AAB was analyzed in more detail using peptides of the G-protein coupled receptors corresponding to the extracellular structures of the receptors which can neutralize the AAB activity. In a similar way the aptamers were tested for their AAB neutralizing capacity.

This functional assay can detect and quantify all human serum AABs and other molecules which target receptors on the cell surface whose sequences are homolog to the human receptors (a prerequisite for the AAB targeting) and which are linked to a protein-cascade which regulates the beating frequency (contractility, chronotropy) of the cells such as the G-protein system.

Preparation of Neonatal Cardiomyocytes

For the preparation of neonatal cardiomyocytes, hearts of 1 to 3 day old rats were removed under sterile conditions and transferred to phosphate buffered saline solution (PBS) containing penicillin/streptomycin. After the separation of the ventricle tissue, it was dissected in pieces and washed twice with 10 ml PBS. Afterwards the dissected ventricle pieces were suspended in 30 ml PBS/0.2% trypsin and incubated for 15 min at 37° C. The trypsination process was stopped adding 5 ml ice-cold heat-inactivated neonatal calf serum. The resulting suspension was centrifuged (130×g, 15 min) and the pellet transferred to 20 ml of SM20-1 medium. Cells were counted while diluting an aliquot of the resulting suspension with the same volume of a trypan blue solution.

$2.4 \times 10^6$ cells suspended in 2.0 ml of glucose containing SM 20-I medium which was equilibrated with humid air and supplemented with 10% heat-inactivated neonatal calf serum, 2 µM fluorodeoxyuridine were transferred to 12.5-cm² Falcon flasks for culturing as monolayers for 4 days at 37° C. The medium was renewed at the first day and afterwards every two days. Experiments were run in the flasks.

Preparation of Serum Samples for AAB Measurement

For the preparation of the IgG fraction, suitable for the AAB measurement, 1 ml of serum and 660 µl saturated ammonium sulfate solution were mixed (final concentration 40% ammonium sulphate), incubated for 18 hours at 4° C. and centrifuged for 15 min at 6,000×g.

The pellet was re-suspended in 750 µl PBS, mixed with 750 µl saturated ammonium sulfate solution (final concentration 50% ammonium sulfate) and centrifuged again. The pellet was suspended in 700 µl PBS and dialyzed against the 100 fold volume of PBS. The resulting IgG fraction contained the AABs and was stored at −20° C. until measurement.

AAB Measurement Principle and Aptamer Testing Setup

Experiments were run in 12.5-cm$^2$ Falcon flasks. Six independent cell clusters which were used for the measurement were marked and the basal cardiomyocyte beating rates at the marked zones were recorded.

For the measurement of the AAB acitivity, prepared IgG samples were added to the cells in a final dilution as indicated in the figure (e.g. AAB 1:50 which corresponds to 40 µl of the IgG solution prepared as described above in 2000 µl cell culture medium). After addition of the IgG samples the flasks were incubated for 60 min at 37° C. and the beating rates of the cardiomyocytes at the marked zones were counted again and the differences to the basal beating rates were calculated which were positive or negative for positive chronotropic or negative chronotropic AAB activity, respectively.

Testing the aptamer effect, the AAB containing IgG samples were preincubated with the corresponding aptamer (SEQ ID No. as indicated in the figure) for 15 min before the mixture was added to the cardiomyocytes. After an incubation time of 60 min (37° C.) the beating frequency was estimated and the difference to the basal beating rate was calculated.

The addition of 2 µl aptamer corresponded to the addition of 100 nM aptamer in the final cell flask (total volume of 2000 µl).

Example 1

The activity of alpha1-adrenoceptor AABs was monitored via recording the increase of the beating rate of neonatale cardiomyocytes (see FIG. 1, column 1: AAB 1:50). Column 2-5, and 7 of FIG. 1 show reduced AAB activity after preincubation of AABs with 100 nM aptamer of the respective sequence (Seq. ID No 2, 3, 10, 15, and 20, respectively). The results of Column 6 of FIG. 1 were obtained by using 100 nM of a control aptamer sequence (Seq. ID No. 19: TCGAGAAAAACTCTCCTCTCCTTCCTTCCTCTCCA) which is not an aptamer sequence according to the present invention.

Example 2

Figure 2:
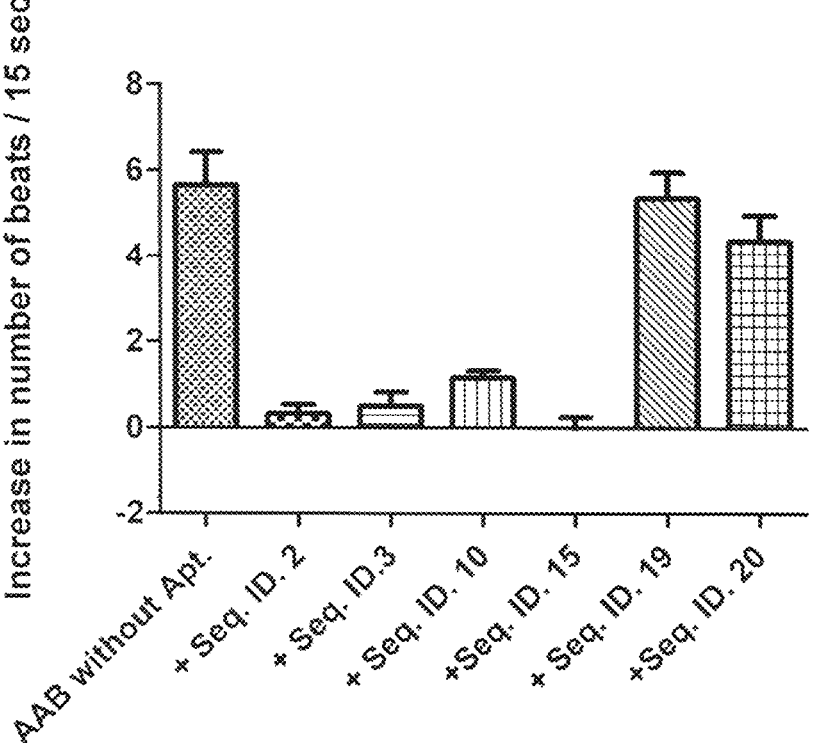
FIG. 2 shows the neutralization of the beta1 adrenoceptor AABs by aptamers (2 µl).

The activity of beta1-adrenoceptor AABs was monitored via recording the increase of the beating rate of neonatale cardiomyocytes (see FIG. 2, column 1: AAB 1:50). Column 2-5, and 7 of FIG. 2 show reduced AAB activity after preincubation of AABs with 100 nM aptamer of the respective sequence (Seq. ID No 2, 3, 10, 15, and 20, respectively). The results of Column 6 of FIG. 2 were obtained by using 100 nM of a control aptamer sequence (Seq. ID No. 19) which is not an aptamer sequence according to the present invention.

Example 3

Figure 3:
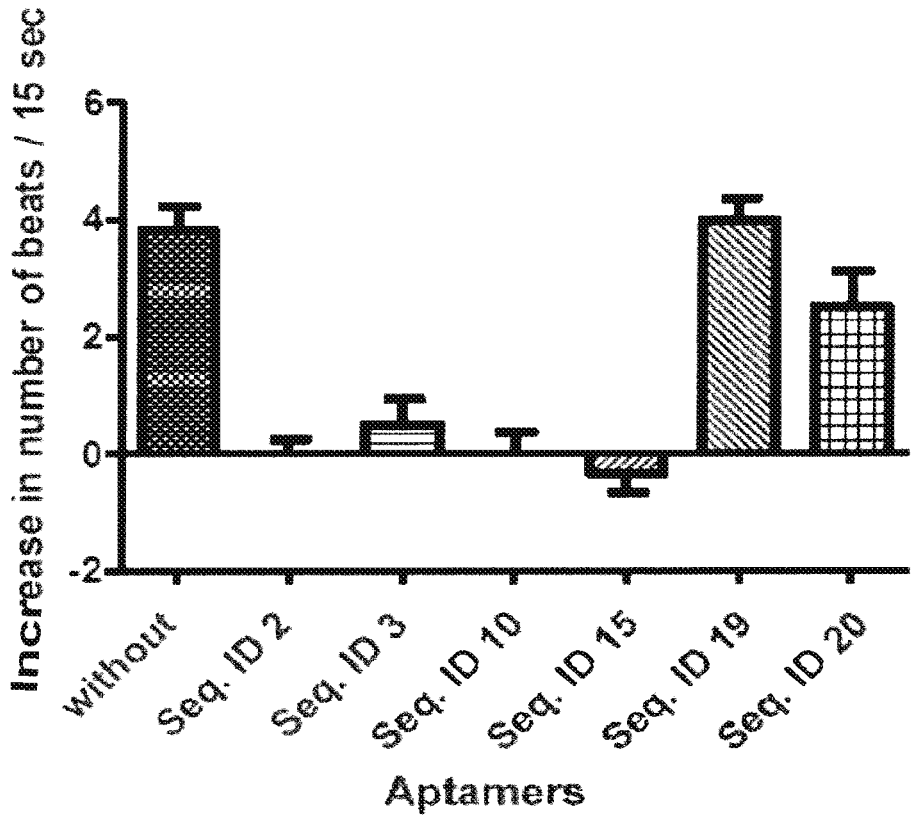
FIG. 3 shows the influence of the aptamers on the effects of the AAB against the PAR1/PAR2 receptors.

The activity of PAR1/PAR2-receptor AABs was monitored via recording the increase of the beating rate of neonatale cardiomyocytes (see FIG. 3, column 1: AAB 1:50). Column 2-5, and 7 of FIG. 3 show reduced AAB activity after preincubation of AABs with 100 nM aptamer of the respective sequence (Seq. ID No 2, 3, 10, 15, and 20, respectively). The results of Column 6 of FIG. 3 were obtained by using 100 nM of a control aptamer sequence (Seq. ID No. 19) which is not an aptamer sequence according to the present invention.

Example 4

Figure 4:
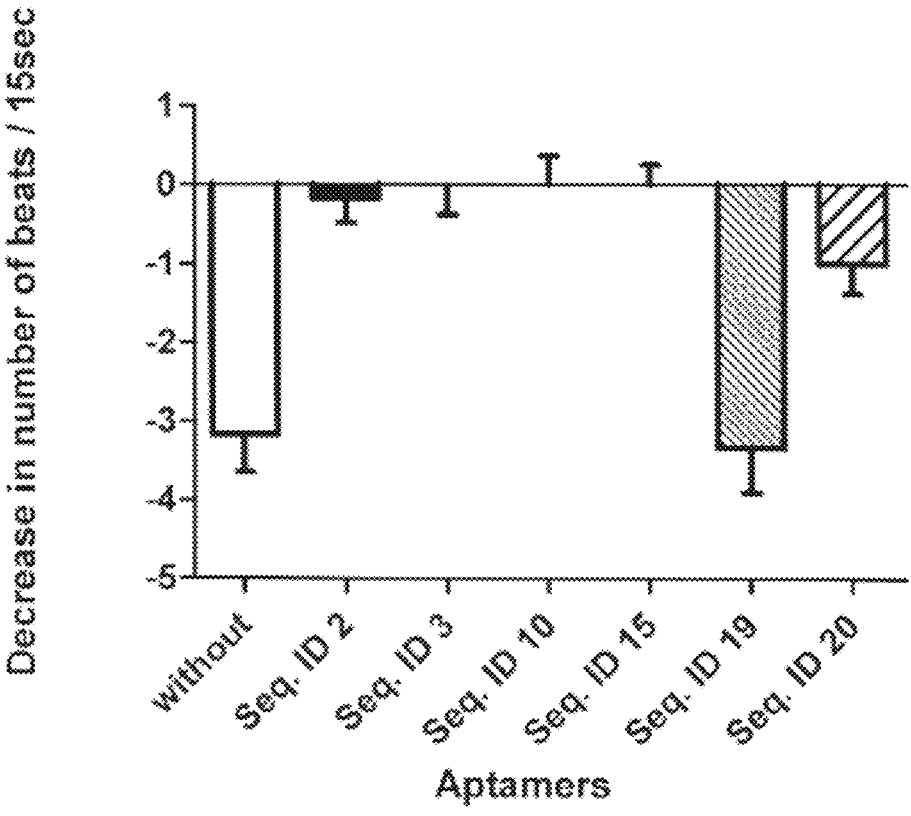
FIG. 4 shows the neutralization of the endothelin 1 ETA receptor AABs by aptamers (2 µl).
Figure 5:
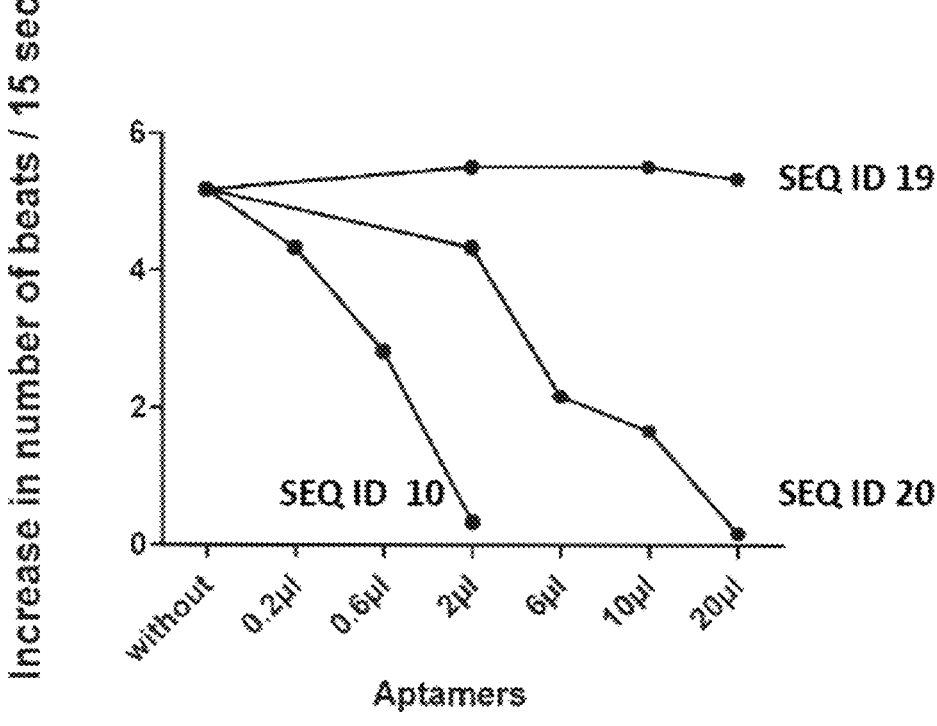
FIG. 5 shows the neutralization of the effect of the β1-adrenoceptor AAB by the aptamers of SEQ ID No. 10, SEQ ID No. 19 and SEQ ID No. 20.

The activity of endothelin 1 ETA-receptor AABs was monitored via recording the decrease of the beating rate of neonatale cardiomyocytes (see FIG. 3, column 1: AAB 1:50). Column 2-5, and 7 of FIG. 3 show reduced AAB activity after preincubation of AABs with 100 nM aptamer of the respective sequence (Seq. ID No 2, 3, 10, 15, and 20, respectively). The results of Column 6 of FIG. 4 were obtained by using 100 nM of a control aptamer sequence (Seq. ID No. 19) which is not an aptamer sequence according to the present invention.

Example 5

The concentration-dependent influence of the aptamers of SEQ ID NO: 10 and SEQ ID NO: 20 on ß1-adrenoceptor AABs was monitored via recording the increase of the beating rate of neonatale cardiomyocytes (data point "without" in the x-axis label corresponds to: AAB 1:50). The curves visualize the dose-dependency of the aptamer effect of aptamer SEQ ID NO 10 and 20. The curve obtained using SEQ ID NO 19 served for control since SEQ ID NO 19 is not an aptamer sequence according to the present invention.

Example 6

Figure 6:
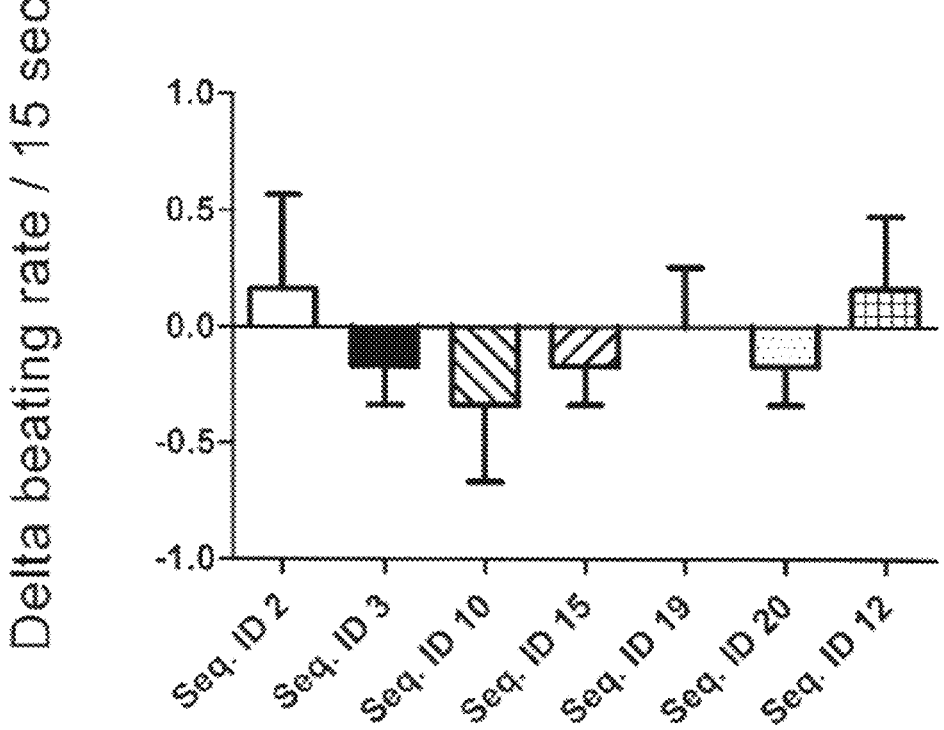
FIG. 6 shows the effects of different aptamers (2 µl) on the beating rate of the cardiomyocytes.

In Example 6, the per se-effects of the aptamers of the invention (SEQ ID NO 2, 3, 10, 15, 20, and 12 shown in column 1,2,3,4,6, and 7, respectively) on the basal beating rate of cardiomyocytes are shown. The results of Column 5 of FIG. 6 were obtained by using a control aptamer sequence (Seq. ID No. 19) which is not an aptamer sequence according to the present invention.

Example 7

Figure 7:
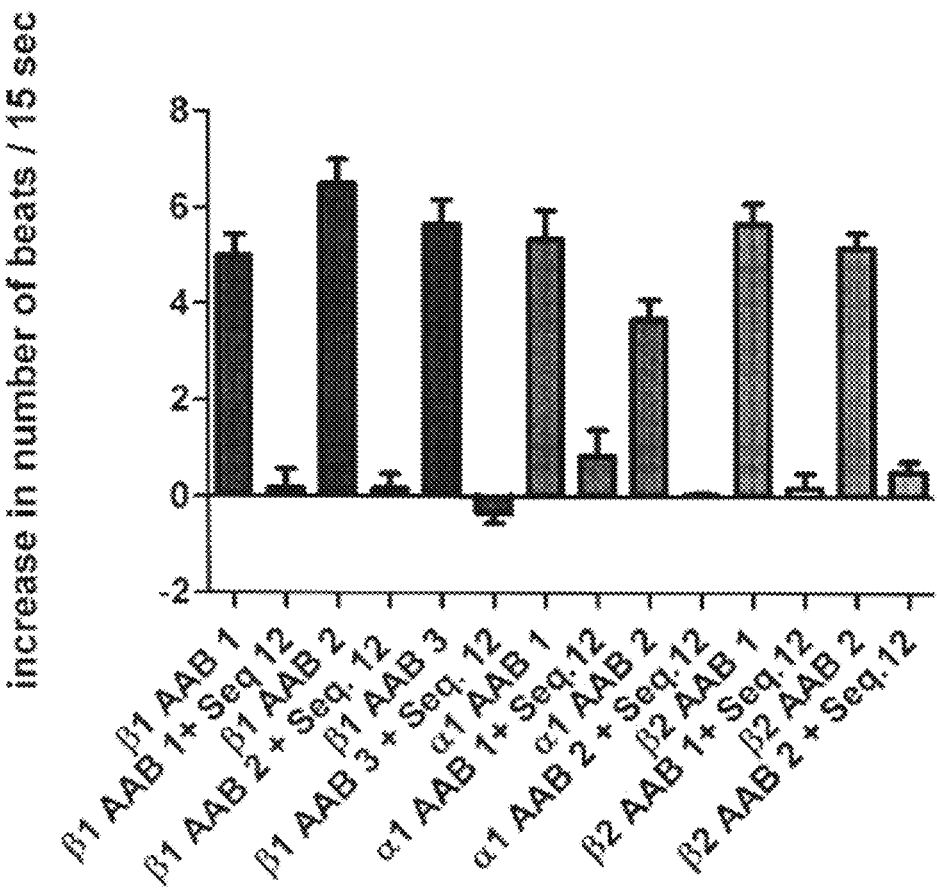
FIG. 7 shows the effects of the aptamer of SEQ ID No. 12 on AABs directed against different G-protein coupled receptors.

The activity of AABs was monitored via recording the increase of the beating rate of neonatal cardiomyocytes (see FIG. 7, column 1: ß1-AAB No. 1, 1:50, column 3: ß1-AAB No. 2, 1:50, column 5: ß1-AAB No. 3, 1:50, column 7: alpha1-AAB No. 1, 1:50, column 8: alphal-AAB No. 2, 1:50, column 11: ß2-AAB No. 1, 1:50, column 13: ß2-AAB No. 2, 1:50). Columns 2, 4, 6, 8, 10, 12, 14 of FIG. 7 show reduced AAB activity (ß1 AAB1, ß1 AAB2, ß1AAB 3, alpha 1 AAB1, alphal AAB 2, ß2-AAB 1, ß2-AAB 2) at 100 nM aptamer of SEQ ID NO: 12. AAB No. 1, 2, and 3 stands for AABs prepared from different patient material.

Example 8

Figure 8:
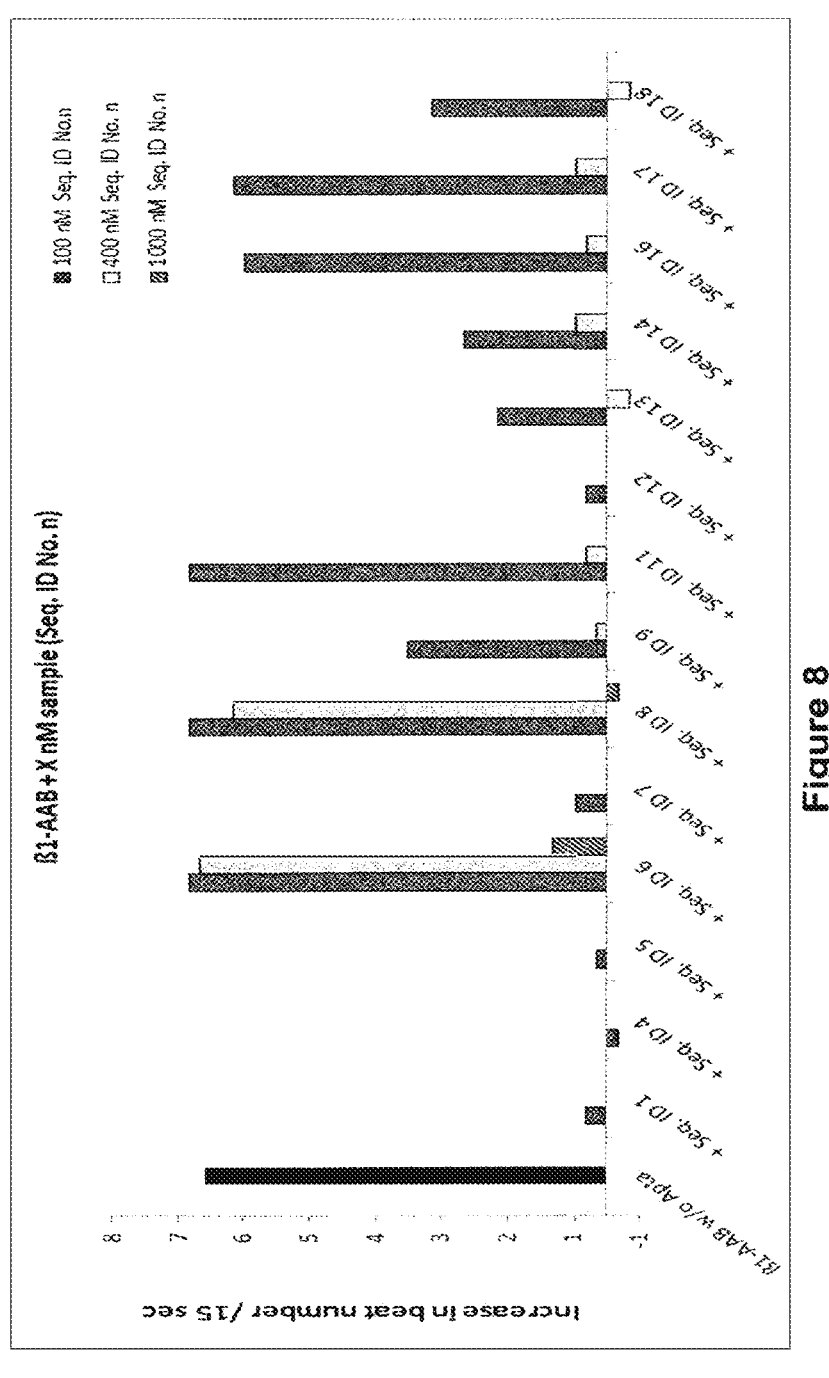
FIG. 8 shows the neutralization of the beta 1 adrenoceptor AABs by 100 nM, 400 nM and 1000 nM of different aptamers (SEQ ID No.: 1, 4 to 9, 11 to 14 and 16 to 18) according to the invention (2 µl).

Example 8 was carried out as in Example 2 above. The activity of beta1-adrenoceptor AABs was monitored by recording the increase of the beating rate of neonatal cardiomyocytes without addition of aptamer (see FIG. 8, column 1: AAB 1:50) and upon addition of aptamers according to the invention. All samples treated with inventive aptamer show reduced AAB activity after preincubation of AABs with 100 nM, 400 nM or 1000 nM aptamer of the respective sequence (Seq. ID No 1, 4 to 7 to 9, 11 to 14 and 16 to 18 in FIG. 8, respectively).

Example 9

Example 9 was carried out as in Example 2 above. The activity of beta1-adrenoceptor AABs was monitored by recording the increase of the beating rate of neonatal cardiomyocytes without addition of aptamer (see FIG. 10, column 1: AAB 1:50) and upon addition of aptamers according to the invention. All samples treated with inventive aptamer show reduced AAB activity after preincubation of AABs with 100 nM aptamer of the respective sequence (Seq. ID No 25 to 45 in FIG. 8, respectively; for mutual identities of these sequences, see FIG. 9). The experiments with aptamers of the sequences SEQ ID No.: 31 to 34, 44 and 45 have further been repeated using 400 nM of each aptamer (see below in Example 10).

Example 10

Example 10 was carried out as in Example 2 above. The activity of beta1-adrenoceptor AABs was monitored by recording the increase of the beating rate of neonatal cardiomyocytes without addition of aptamer (see FIG. 11, column 1: AAB 1:50) and upon addition of aptamers according to the invention. All samples treated with inventive aptamer show reduced AAB activity after preincubation of AABs with 400 nM aptamer of the respective sequence (Seq. ID No 31 to 34, 44 and 45, respectively).

Example 11

Example 11 was carried out as in Example 2 above. The activity of beta1-adrenoceptor AABs was monitored by recording the increase of the beating rate of neonatal cardiomyocytes without addition of aptamer (see FIG. 12, column 1: AAB 1:50) and upon addition of control sequences not according to the invention. All samples treated with control sequences show unaffected AAB activity after preincubation of AABs with 100 nM, 400 nM or 1000 nM control of the respective sequence (Seq. ID No 46: 5'-ACCTCTCCTTCCTTCCTCTCCTCT-CAAAAAGAGCT-3', SEQ ID No 47: 5'-TCCCATCTATT-ATTTTTCTTCTAATCATC-3', SEQ ID No 48: 5'-ATCT-CATGAACGTAAAGCCATTCAAACG-3', SEQ ID No 49: 5'-ACACTAGTAGCCACACTGAG-3', SEQ ID No 50: 5'-CCTGCCCCCTAAA-3', respectively).

Example 12

Example 12 was carried out as in Example 2 above. The activity of beta1-adrenoceptor AABs isolated from patients suffering from depression or Chagas' cardiomyopathy (from left to right in FIG. 13) was monitored by recording the increase of the beating rate of neonatal cardiomyocytes without addition of aptamer (see FIG. 13, column 1: AAB 1:50) and upon addition of 100 nM of aptamer of SEQ ID No: 12 according to the invention. The samples treated with inventive aptamer show reduced AAB activity after preincubation of AABs with 100 nM of SEQ ID No: 12 in comparison to the control sample to which no aptamer has been added.

Example 13

Example 13 was carried out as in Example 12 above, wherein in this Example the activity of beta2-adrenoceptor AABs isolated from patients suffering from glaucoma, schizophrenia, Chagas' cardiomyopathy, hemolytic-uremic syndrome (EHEC) or Alzheimer's disease (from left to right in FIG. 14) in the absence or presence of 100 nM of the inventive aptamer of SEQ ID No.: 12 was monitored.

Example 14

Example 14 was carried out as in Example 12 above, wherein in this Example the activity of AT1 AABs isolated from patients suffering from alopecia, kidney allograft rejection or high blood pressure at kidney disease (from left to right in FIG. 15) in the absence or presence of 100 nM of the inventive aptamer of SEQ ID No.: 12 was monitored.

Example 15

Example 15 was carried out as in Example 12 above, wherein in this Example the activity of ETA AABs isolated from patients suffering from pulmonary arterial hypertension, Raynaud's disease, angina pectoris or high blood pressure at kidney disease (from left to right in FIG. 16) in the absence or presence of 100 nM of the inventive aptamer of SEQ ID No.: 12 was monitored.

Example 16

Example 16 was carried out as in Example 12 above, wherein in this Example the activity of alpha 1 AABs isolated from patients suffering from pulmonary arterial hypertension, chemotherapy, multiple sclerosis, alopecia, alopecia areata, hemolytic-uremic syndrome (EHEC), Sjögren's syndrome, Alzheimer's disease, neurodermatitis, Diabetes mellitus Type I or psoriasis (from left to right in FIG. 17) in the absence or presence of 100 nM of the inventive aptamer of SEQ ID No.: 12 was monitored.

Example 17

Example 17 was carried out as in Example 12 above, wherein in this Example the activity of PAR AABs isolated from patients suffering from Raynaud's disease, angina pectoris or Sjögren's syndrome (from left to right in FIG. 18) in the absence or presence of 100 nM of the inventive aptamer of SEQ ID No.: 12 was monitored.

Example 18

Example 18 was carried out as in Example 12 above, wherein in this Example the activity of MAS AABs isolated from patients suffering from chemotherapy, multiple sclerosis or Diabetes mellitus Type I (from left to right in FIG. 19) in the absence or presence of 100 nM of the inventive aptamer of SEQ ID No.: 12 was monitored.

Example 19

Figure 20:
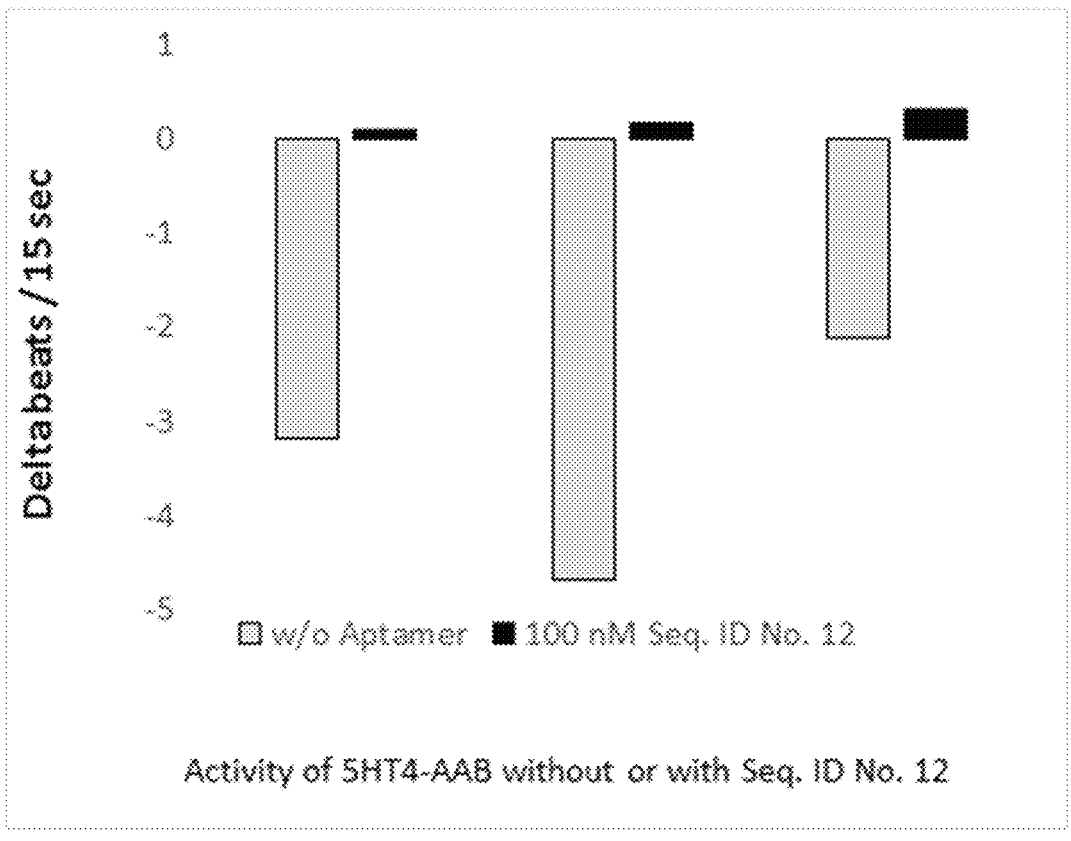
FIG. 20 shows the activity of 5HT4 AABs isolated from patients suffering from depression, schizophrenia or migraine/Parkinson's disease (from left to right) in the absence or presence of 100nM of the inventive aptamer of SEQ ID No.: 12.
Figure 21:
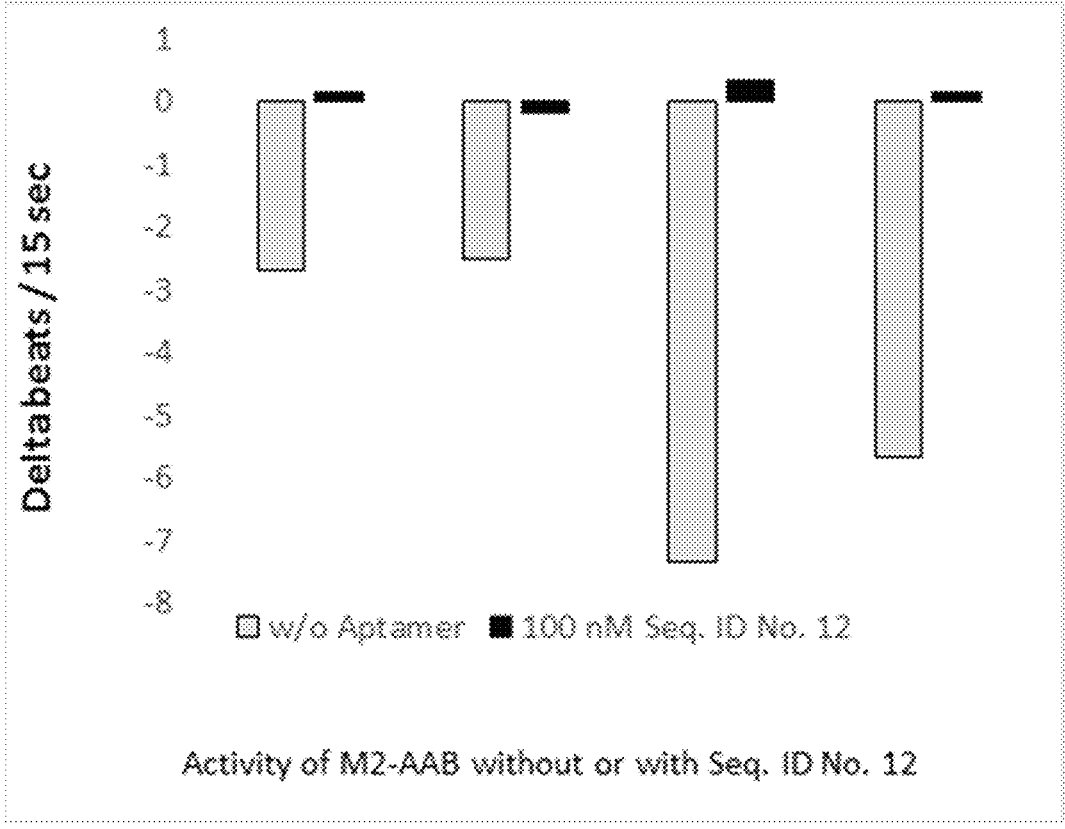
FIG. 21 shows the activity of M2 AABs isolated from patients suffering from Chagas' cardiomyopathy, alopecia areata, migraine/Parkinson's disease or Sjögren's syndrome (from left to right) in the absence or presence of 100 nM of the inventive aptamer of SEQ ID No.: 12.

Example 19 was carried out as in Example 12 above, wherein in this Example the activity of 5HT4 AABs isolated from patients suffering from depression, schizophrenia or migraine/Parkinson's disease (from left to right in FIG. 20)

in the absence or presence of 100 nM of the inventive aptamer of SEQ ID No.: 12 was monitored.

Example 20

Example 20 was carried out as in Example 12 above, wherein in this Example the activity of M2 AABs isolated from patients suffering from Chagas' cardiomyopathy, alopecia areata, migraine/Parkinson's disease or Sjögren's syndrome (from left to right in FIG. 21) in the absence or presence of 100 nM of the inventive aptamer of SEQ ID No.: 12 was monitored.

---

The invention claimed is:

1. A method of treating an autoimmune disease comprising administering an effective amount of an aptamer to autoantibodies against a human G-protein coupled receptor in the blood or constituents thereof of a human patient suffering from the autoimmune disease, wherein the autoimmune disease is dilated cardiomyopathy (DCM) or Chagas' cardiomyopathy, wherein said autoantibodies are specific for the G-protein coupled receptor and have been determined to be present in the serum of said patient suffering from said autoimmune disease, wherein the G-protein coupled receptor is an adrenergic alpha-1 receptor, wherein the aptamer binds said autoantibodies and inhibits specific binding of said autoantibodies to the human G-protein coupled receptor, and wherein the aptamer comprises a nucleotide sequence of 5'-GGTGGTGGTGGTTGTGGTGGTGGTGG-3' (SEQ ID No: 12).

2. The method of claim 1, wherein the aptamer is administered to the autoantibodies in the patient in the form of a pharmaceutical composition comprising at least the aptamer and at least one pharmaceutically acceptable excipient.

3. The method of claim 1, wherein the blood or constituents thereof is removed from the patient and run through an apheresis column, wherein the aptamer is used as selective ingredient in the apheresis column for specifically separating out the autoantibodies which are specifically targeted by the aptamer, before the blood or constituents thereof is returned to the patient.

4. The method of claim 1, wherein the autoimmune disease is dilated cardiomyopathy (DCM).

5. The method of claim 1, wherein the autoimmune disease is Chagas' cardiomyopathy.

* * * * *

```
                        SEQUENCE LISTING

<160> NUMBER OF SEQ ID NOS: 81

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 1
gttgtttggg gtgg                                                     14

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 2
gttgtttggg gtggt                                                    15

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 3
ggttggggtg ggtggggtgg gtggg                                         25

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 4
tttggtggtg gtggttgtgg tggtggtg                                      28

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      aptamer sequence
```

-continued

```
<400> SEQUENCE: 5
tttggtggtg gtggttgtgg tggtggtgg                                      29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 6
tttggtggtg gtggttttgg tggtggtgg                                      29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 7
tttggtggtg gtggtggtgg tggtggtgg                                      29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 8
tttggtggtg gtggtttggg tggtggtgg                                      29

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 9
tggtggtggt ggt                                                       13

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 10
ggtggtggtg g                                                         11

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 11
```
ggtggttgtg gtgg                                                              14

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 12
ggtggtggtg gttgtggtgg tggtgg                                                 26

<210> SEQ ID NO 13
<211> LENGTH: 56
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 13
ggtggtggtg gttgtggtgg tggtggttgt ggtggtggtg gttgtggtgg tggtgg              56

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 14
ggtggttgtg gtggttgtgg tggttgtggt gg                                          32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 15
tttggtggtg gtggttgtgg tggtggtggt tt                                          32

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 16
ggtggtggtg ttgtggtggt ggtggttt                                              28

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 17

-continued

```
tttggtggtg gtggtgtggt ggtggtgg                                28

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 18
tggtggtggt                                                    10

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 19
tcgagaaaaa ctctcctctc cttccttcct ctcca                        35

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 20
ttagggttag ggttagggtt aggg                                    24

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 21
gactgtaccg aggtgcaagt actcta                                  26

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 22
ggttggtgtg gttgg                                              15

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 23
ggttggtgtg gt                                                 12
```

-continued

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 24
cgcctaggtt gggtagggtg gtggcg                                        26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 25
gcggtggtgg gatgggttgg atccgc                                        26

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 26
gggtcgggat ctagggtcag g                                             21

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 27
ggtgggtcgg tagggttt                                                 18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 28
ttggctggat cggacggt                                                 18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 29
ggtcgggttc ggtggtta                                                 18

-continued

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 30
gggatcggtt cggtaggtgg gtgggttgg                                        29

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 31
ggccggcgcg gccgg                                                       15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 32
ggaaggatcg gaagg                                                       15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 33
ggtaggctcg gtagg                                                       15

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 34
ggatggttag gatgg                                                       15

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 35
ccgtcggtcc gttcggtatt tttttctggg tggctgagga tcg                       43

-continued

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 36
gggttggtcc gttgggtatt tttttatggg ttgcctggtt ggg                         43

<210> SEQ ID NO 37
<211> LENGTH: 47
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 37
tcccatcggg tagggttatt tgggttctgg gtggctgagg atcgatc                     47

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 38
tggcggtggt                                                              10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 39
tggaggtgga                                                              10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 40
aggtggtgga                                                              10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 41
aggtggcgga                                                              10

<210> SEQ ID NO 42

```
<211> LENGTH: 26
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 42
gtggtggtgg tgttggtggt ggtggg                                              26

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 43
tgggttgggt tgttgttgtt gggttgggt                                           29

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 44
ggtggtggtg gtggttggtt tttggttggt ggtggtggtg g                            41

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      aptamer sequence

<400> SEQUENCE: 45
ctggggttgg gtttggtttt gttttggttt gggttggggt c                            41

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      control sequence

<400> SEQUENCE: 46
acctctcctt ccttcctctc ctctcaaaaa gagct                                   35

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: Synthetic
      control sequence

<400> SEQUENCE: 47
tcccatctat tattttttctt ctaatcatc                                          29

<210> SEQ ID NO 48
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      control sequence

<400> SEQUENCE: 48
atctcatgaa cgtaaagcca ttcaaacg                                             28

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      control sequence

<400> SEQUENCE: 49
acactagtag ccacactgag                                                      20

<210> SEQ ID NO 50
<211> LENGTH: 13
<212> TYPE: DNA
<213> ORGANISM: Artificial Sequence
<220> FEATURE:
<223> OTHER INFORMATION: Description of Artificial Sequence: Synthetic
      control sequence

<400> SEQUENCE: 50
cctgccccct aaa                                                             13

<210> SEQ ID NO 51
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggtggtggtg gt                                                              12

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggtggtggtg gttgg                                                           15

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggtggtggtg gttggtgg                                                        18

<210> SEQ ID NO 54
<211> LENGTH: 21
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 54
ggtggtggtg gttggtggtg g                                                    21

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggtggtggtg gttggtggtg gtgg                                                 24

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggtggtggtg gttggtggtg gt                                                   22

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggtggtggtg gttggtggt                                                       19

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggtggtggtg gttggt                                                          16

<210> SEQ ID NO 59
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggtggtggtg gtt                                                             13

<210> SEQ ID NO 60
<211> LENGTH: 12
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 60
ggttggggtg gg                                                        12

<210> SEQ ID NO 61
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggttggggtg ggt                                                       13

<210> SEQ ID NO 62
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggttggggtg ggtggg                                                    16

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggttggggtg ggtgggg                                                   17

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggttggggtg ggtggggt                                                  18

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ggttggggtg ggtggggtgg g                                              21

<210> SEQ ID NO 66
<211> LENGTH: 22
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 66
ggttggggtg ggtggggtgg gt                                             22

<210> SEQ ID NO 67
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tttggtggtg g                                                         11

<210> SEQ ID NO 68
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tttggtggtg gt                                                        12

<210> SEQ ID NO 69
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tttggtggtg gtgg                                                      14

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tttggtggtg gtggt                                                     15

<210> SEQ ID NO 71
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tttggtggtg gtggtt                                                    16

<210> SEQ ID NO 72
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
tttggtggtg gtggttg                                                    17

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tttggtggtg gtggttgt                                                   18

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tttggtggtg gtggttgtgg                                                 20

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tttggtggtg gtggttgtgg t                                               21

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tttggtggtg gtggttgtgg tgg                                             23

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tttggtggtg gtggttgtgg tggt                                            24

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 78
tttggtggtg gtggttgtgg tggtgg                                                      26

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tttggtggtg gtggttgtgg tggtggt                                                     27

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tttggtggtg gtggttgtgg tggtggtggt                                                  30

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tttggtggtg gtggttgtgg tggtggtggt t                                                31
```